United States Patent
Kim et al.

(10) Patent No.: US 10,668,061 B2
(45) Date of Patent: Jun. 2, 2020

(54) MOUSE WITH D4R IRNA IN THE INTERCALATING CELL MASS OF THE AMYGDALA

(71) Applicant: POSTECH ACADEMY-INDUSTRY FOUNDATION, Pohang (KR)

(72) Inventors: Joung-Hun Kim, Seoul (KR); Joo Han Lee, Pohang (KR); BumJin Ko, Pohang (KR); Oh-Bin Kwon, Daegu (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 15/466,956

(22) Filed: Mar. 23, 2017

(65) Prior Publication Data
US 2018/0064707 A1    Mar. 8, 2018

(30) Foreign Application Priority Data
Sep. 5, 2016    (KR) .................. 10-2016-0113603

(51) Int. Cl.
A01K 67/027    (2006.01)
A61K 31/495    (2006.01)
A61K 49/00    (2006.01)
C12N 15/00    (2006.01)

(52) U.S. Cl.
CPC ........ *A61K 31/495* (2013.01); *A01K 67/0276* (2013.01); *A61K 49/0008* (2013.01); *A01K 2207/05* (2013.01); *A01K 2217/206* (2013.01); *A01K 2227/105* (2013.01); *A01K 2267/035* (2013.01); *A01K 2267/0356* (2013.01); *C12N 2750/14143* (2013.01)

(58) Field of Classification Search
USPC .................................. 800/8, 18, 21
See application file for complete search history.

(56) References Cited

U.S. PATENT DOCUMENTS

2008/0311657 A1* 12/2008 Levite ............... A61K 31/55 435/372.3
2016/0220563 A1*  8/2016 Bhide ............... A61K 31/4545
2016/0317474 A1* 11/2016 Aung ............... A61K 31/137

OTHER PUBLICATIONS

National Institute of Mental Health description of PTSD, updated 2016.*
Goswami (Frontiers in Neurosci., May 2013, vol. 7, Article 89, p. 1-14).*
Rubinstein (Cell, 1997, vol. 90, p. 991-1001).*
Strange (Dopamine Receptors Scientific Review, 2013).*
"DSM-5 criteria for PTSD" (National Center for PTSD, US Department of Veterans Services, 2018).*
Oh-Bin Kwon et al., "Dopamine Regulation of Amygdala Inhibitory Circuits for Expression of Learned Fear", Neuron 88, pp. 378-389, Oct. 21, 2015.
Joo Han Lee et al., "Dopamine-dependent synaptic plasticity in an amygdala inhibitory circuit controls fear memory expression", BMB Rep. vol. 49(1), pp. 1-2, Jan. 2016.
Stephanie C. Dulawa et al., "Dopamine D4 Receptor-Knock-Out Mice Exhibit Reduced Exploration of Novel Stimuli", The Journal of Neuroscience, vol. 19(21), pp. 9550-9556, Nov. 1, 1999.
Sonal Goswami et al., "Animal models of post-traumatic stress disorder: face validity", Frontiers in Neuroscience, vol. 7, Article 89, May 31, 2013.
KIPO, Office Action of Application No. 10-2016-0113603 which corresponds to the application, dated Feb. 20, 2018.
B. Ko et al., "Dopamine-Mediated Regulation of Amygdala Inhibitory Circuits for Expression of Fear Memory", 10th Fens Poster Presentation VII, Board No. B032, Jul. 6, 2016.
KIPO, Office Action of KR 10-2016-0113603 dated on Dec. 6, 2018.

* cited by examiner

*Primary Examiner* — Michael C Wilson
(74) *Attorney, Agent, or Firm* — Lex IP Meister, PLLC

(57) ABSTRACT

Provided are a posttraumatic stress disorder (PTSD) animal model in which dopamine receptor subtype 4 (D4R) is damaged or deficient, a method for preparing the same, a method for screening a drug for treating PTSD using the same, and a pharmaceutical composition for treating PTSD comprising a drug detected by the screening method. As it is identified that a specific type of dopamine receptor is associated with a mechanism for fear memory expression induced by long-term depression (LTD), the understanding of pathogenesis of PTSD may be heightened, the animal model exhibiting similar clinical conditions of PTSD and the method for preparing the same may be applied in analyses for stability and effectiveness of a therapeutic agent for PTSD and screening of a therapeutic drug. Further, an agonist of D4R contained in the composition has been approved by the US FDA and clinically used for psychiatric diseases such as schizophrenia, and thus may be immediately used for clinical applications for PTSD symptoms.

2 Claims, 34 Drawing Sheets

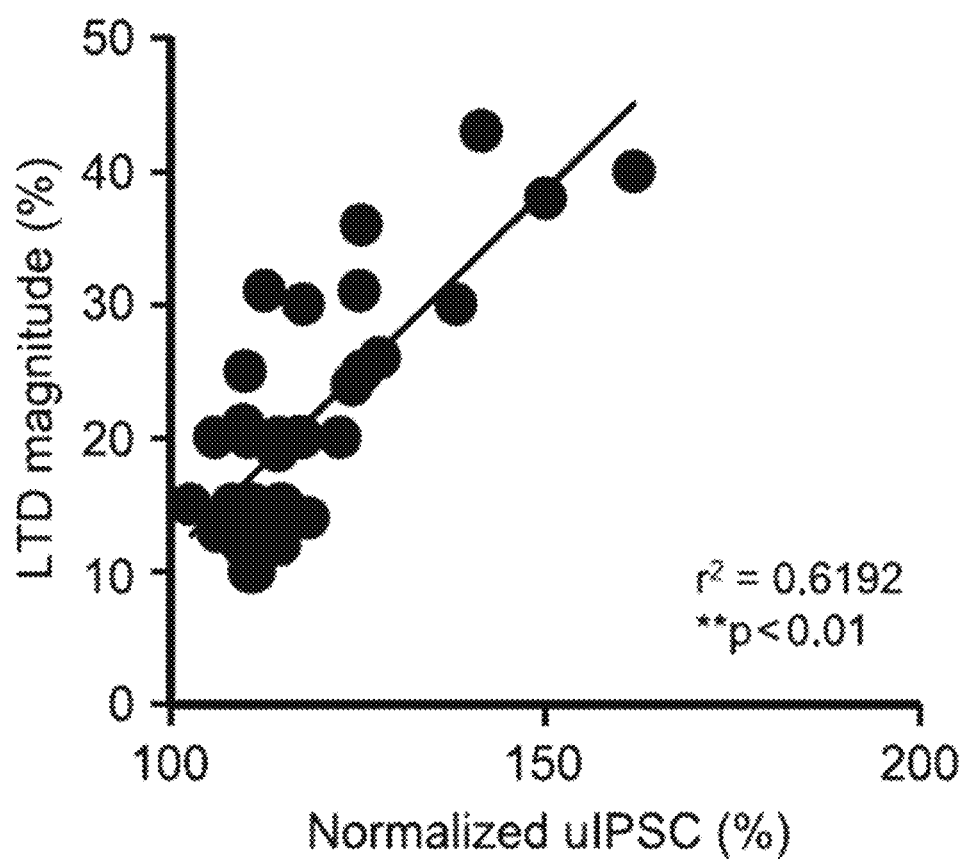

MOUSE WITH D4R IRNA IN THE INTERCALATING CELL MASS OF THE AMYGDALA

CROSS-REFERENCE TO RELATED APPLICATION

This application claims priority to and the benefit of Korean Patent Application No. 2016-0113603, filed on Sep. 5, 2016, the disclosure of which is incorporated herein by reference in its entirety.

BACKGROUND

1. Field of the Invention

The present invention relates to a posttraumatic stress disorder (PTSD) animal model in which dopamine receptor subtype 4 (D4R) is damaged or deficient, a method for preparing the same, a method for screening a PTSD drug using the same, and a pharmaceutical composition for treating PTSD, which comprises a drug detected by the screening method.

2. Discussion of Related Art

As a component of limbic system, the amygdala is a brain region critical for acquisition and expression of conditioned fear and located at the end of hippocampus. It has nuclei more than ten, including basolateral nuclei, corticomedial nuclei and central nucleus (CeA). Among several nuclei that constitute the amygdala complex, it is the lateral nucleus (LA) that receives sensory inputs during fear conditioning, and after being associated in the LA, the signals are transmitted to the central nucleus (CeA) either directly or via the basal nucleus. The intercalated cell masses (ITCs), which are situated between the amygdala nuclei encompassing the dorsal, ventral, and lateral clusters, appear to play a regulatory role in fear-related behavior by controlling the signal transfer between those amygdala nuclei. Thus, saponin-mediated lesions of ITCs or pharmacological inhibition of basolateral amygdale (BLA) inputs to ITCs interferes with extinction of fear memory. Although extinction of fear memory strengthens the excitatory inputs from the BLA to the ventral ITC, it remains unclear whether synaptic plasticity arising at the dorsal ITC can modulate fear acquisition and expression.

The dorsal ITC residing between the LA and CeA receives glutamatergic inputs from LA as well as from cortical regions, and it provides GABAergic inhibitory outputs to the lateral sector of the CeA and the ventral ITC. By contrast, the ventral ITC receives its major inputs from the basal nucleus of the amygdala and sends projections to the medial sector of the CeA. The differences in connectivity of individual ITCs suggest that each ITC can play distinct roles in the regulation of fear behavior. Indeed, it has been proposed that the dorsal ITC regulates fear expression while the ventral ITC controls fear extinction. This raises the possibility that synaptic plasticity in the dorsal ITC could modify fear-related signaling from the LA to the CeA and the ensuing behavior and that deficit in the plastic capabilities of the dorsal ITC could potentially contribute to fear-related psychiatric diseases such as posttraumatic stress disorder (PTSD).

By modulating the activity of amygdala neurons, dopaminergic neurons can control the expression of fear memory. Consistent with this notion, a subset of dopaminergic neurons is robustly activated on the presentation of aversive stimuli, and their firing rates positively correlate with the intensity or salience of the stimulus. Dopamine (DA) gates synaptic plasticity in the amygdala and ultimately controls acquisition of fear memory by reducing feed-forward inhibition to LA projection neurons by means of DA-mediated increases in disynaptic inhibitory postsynaptic currents (IPSCs) in the local interneurons. As with the local interneurons within the BLA, the output of ITCs also can be regulated by DA. Although the dorsal ITC receives potent dopaminergic inputs, the DA-dependent long-term synaptic plasticity in the dorsal ITC circuit has not been explored. Meanwhile, although target-specific methods have been developed to reduce side effects in treatment of diseases with drugs, techniques used for the brain are still very limited. In current situation in which the number of patients classified as having mental disorders continues to grow, it is necessary to find a function/site-specific target in order to minimize drug side effects.

In particular, Post-traumatic stress disorder (PTSD) is a prevalent and highly debilitating psychiatric disorder that is notoriously difficult to treat. PTSD is characterized by flashbacks, emotional numbness, and insomnia, and is associated with mental health comorbidities, such as depression. PTSD can result from a catastrophic and threatening event, e.g., a natural disaster, wartime situation, accident, domestic abuse, or violent crime. Symptoms typically develop within three months, but can emerge years after the initial trauma. Also, PTSD is particularly prevalent among combat veterans, and it is reported that an estimated 17% of Iraqi combat veterans developed PTSD. There has been a growing demand for a medication showing a great treatment effects and having fewer side effects than existing drugs, but so far no such medication has been presented.

SUMMARY OF THE INVENTION

The inventors found that inhibitory synaptic plasticity regulated by D4R serves to limit the expression of learned fear and thus can regulate symptoms such as fear generalization which is one of the core symptoms in PTSD, and PTSD symptoms can be reduced by using an agonist of D4R.

Accordingly, the present invention is directed to providing a dopamine receptor subtype 4-damaged or deficient PTSD animal model, a method for preparing the same, a method for screening a PTSD drug using the same, and a pharmaceutical composition for treating PTSD, which comprises a drug detected by the screening method.

However, technical problems to be solved in the present invention are not limited to the above-described problems, and other problems which are not described herein will be fully understood by those of ordinary skill in the art from the following descriptions.

The present invention provides a D4R-damaged or deficient PTSD animal model, excluding humans.

In one embodiment of the present invention, the damage or deficiency of D4R may occur in the dorsal intercalated cell masses (ITCs) of the amygdala.

In another embodiment of the present invention, long-term depression (LTD) is inhibited by D4R damage or deficiency.

In still another embodiment of the present invention, excessive fear responses are induced by the LTD inhibition.

Also, the present invention provides a method for preparing the PTSD animal model.

In one embodiment of the present invention, the preparation method comprises performing knock-down or knock-out of a D4R gene.

Also, the present invention provides a method for screening a drug for preventing or treating PTSD using the animal model.

In one embodiment of the present invention, the screening method comprises (a) treating the PTSD animal model with a candidate drug; and (b) measuring D4R activity in the amygdala.

In another embodiment of the present invention, the method further comprises (c) selecting the treated drug as a therapeutic drug when D4R is activated.

In still another embodiment of the present invention, LTD is induced by the D4R activation.

In yet another embodiment of the present invention, fear responses are inhibited by the LTD.

In yet another embodiment of the present invention, the therapeutic drug is a D4R agonist.

In yet another embodiment of the present invention, the agonist is N-([4-(2-cyanophenyl)piperazine-1-yl]methyl)-3-methylbenzamide (PD-168077).

Also, the present invention provides a pharmaceutical composition for preventing or treating PTSD, which comprises the drug detected by the screening method as an active ingredient.

In one embodiment of the present invention, the drug is a D4R agonist.

In another embodiment of the present invention, the D4R agonist is one or more selected from the group consisting of the following.

PD 168077 maleate: N-(methyl-4-(2-cyanophenyl)piperazinyl-3-methylbenzamide maleate A 412997 dihydrochloride: N-(3-methylphenyl)-4-(2-pyridinyl)-1-piperidineacetamide ABT 724 trihydrochloride: 2-[[4-(2-pyridinyl)-1-piperazinyl]methyl]-1H-benzimidazole trihydrochloride WAY 100635 maleate: N-[2-[4-(2-methoxyphenyl)-1-piperazinyl]ethyl]-N-2-pyridinylcyclohexanecarboxamide maleate Ro 10-5824 dihydrochloride: 5-[(3,6-dihydro-4-phenyl-1(2H)-pyridinyl)methyl]-2-methyl-4-pyrimidinamine dihydrochloride In still another embodiment of the present invention, the D4R agonist is N-([4-(2-cyanophenyl)piperazine-1-yl]methyl)-3-methylbenzamide (PD-168077).

In yet another embodiment of the present invention, the D4R agonist activates the receptor to induce LTD.

In yet another embodiment of the present invention, the LTD takes place in the dorsal ITCs of the amygdala.

In yet another embodiment of the present invention, fear responses are inhibited by the LTD.

Also, the present invention provides a method for treating PTSD, which comprises administering a D4R agonist into a subject.

Also, the present invention provides a use of a D4R agonist to treat PTSD.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1a to 1e show diagrams illustrating that synaptic plasticity in the dorsal ITC synapses is controlled by fear conditioning, in which FIG. 1a shows the dorsal ITC neurons that are identified spatially and morphologically;

FIG. 1b is a schematic diagram illustrating a process of obtaining whole cell patch recordings of excitatory postsynaptic potentials (EPSPs) while electrically stimulating the lateral nucleus of the amygdala;

FIG. 1c shows synaptic plasticity in the amygdala assessed according to a spike-timing dependent plasticity (STDP) protocol, with respect to mice having no fear memories and mice that undergo weak/strong fear conditioning;

FIG. 1d is a schematic diagram of optogenetic analysis for evaluating synaptic plasticity in a specific pathway exhibiting LTD; and FIG. 1e shows synaptic plasticity in the lateral nucleus-dorsal ITC pathway in the amygdala, assessed with STDP-like light stimulation;

FIG. 2a to 2d show enhanced inhibition with respect to the dorsal ITC neurons after weak fear conditioning, in which FIG. 2a shows miniature inhibitory postsynaptic currents (mIPSCs) measured after fear conditioning;

FIG. 2b shows miniature excitatory postsynaptic currents (mEPSCs) measured after fear conditioning;

FIG. 2c shows biphasic PSPs (EPSP/IPSP) caused by stimulation of the lateral nucleus in the amygdala; and FIG. 2d shows the input-output curves for disynaptic IPSPs after weak/strong fear conditioning;

FIG. 3a to 3h show dopamine (DA)-dependent LTD by activation of D4R, in which

FIG. 3a shows DA-induced LTD during STDP stimulation in the dorsal ITC neurons;

FIG. 3b shows DA-dependent LTD induced by light stimulation after rAAV5-CamKIIα-hChR2-eYFP is infused into the lateral nucleus in the amygdala;

FIG. 3c shows assessment of DA-dependent LTD by treatment with dopamine receptor subtype-specific antagonists;

FIG. 3d shows assessment of DA-dependent LTD by treatment with dopamine receptor subtype-specific agonists;

FIG. 3e shows assessment of DA-dependent LTD in D4R-knockout mice;

FIG. 3f shows that LTD induced after weak fear conditioning is inhibited by treatment with D4R-specific antagonists;

FIG. 3g shows subcellular localization of D4R in wild-type mice, observed by post-embedding immuno-gold transmission electron microscopy; and FIG. 3h shows subcellular localization of D4R in D4R-knockout mice, observed by post-embedding immuno-gold transmission electron microscopy;

FIG. 4a to 4h show feed-forward inhibition signals increased by DA-dependent LTD in the dorsal ITC, in which FIG. 4a shows that mIPSC frequency is increased by the induction of DA-dependent LTD;

FIG. 4b shows that DA-dependent LTD does not affect mEPSCs;

FIG. 4c shows that disynaptic IPSPs are increased by the induction of DA-dependent LTD;

FIG. 4d shows synaptic responses from the dorsal ITC neurons obtained by interleaving stimulation of the lateral nucleus or dorsal ITC in the amygdala;

FIG. 4e shows that IPSCs are increased, but EPSCs are decreased when DA-dependent LTD is induced;

FIG. 4f shows unitary IPSCs (uIPSCs) in the post-synaptic neurons;

FIG. 4g shows that uIPSCs are increased in the post-synaptic neurons after the induction of D4R-dependent LTD; and FIG. 4h shows a positive correlation between the increase in uIPSCs and LTD magnitude;

FIG. 5a to 5c show that fear behavior is regulated by D4R activity in the dorsal ITC neurons, in which FIG. 5a is an experimental schematic diagram for evaluating the influence of the infusion of a D4R antagonist (L-745870) into the dorsal ITC on the expression of fear behavior after weak fear conditioning, and FIG. 5b shows the experimental result;

FIG. 5c is an experimental scheme for evaluating the influence on the expression of fear behavior after weak fear conditioning using a genetic method for depleting D4R from inhibitory neurons of the dorsal ITC.

FIG. 6a to 6d show that the expression of fear memory is increased when LTD is optogenetically inhibited, in which FIG. 6a shows that LTD is inhibited in the dorsal ITC 24 hours after fear recall is given to fear-learned mice;

FIG. 6b shows that DA-dependent LTD is inhibited by optogenetically manipulating the lateral nucleus-dorsal ITC pathway of the amygdala after weak fear conditioning;

FIG. 6c is a schematic diagram illustrating in vivo optogenetic manipulation and the design for behavior tests; and FIG. 6d shows that, when the optogenetic TBS is applied to the dorsal ITC, rAAV5-CamKIIα-hChR2-eYFP-infused mice exhibit significant increases in fear behavior responses, compared to the control;

FIG. 7a to 7e show impaired LTD in the dorsal ITC of PTSD-like animal models, in which FIG. 7a shows cue-induced fear responses measured by administering corticosterone (CORT) to mice undergoing weak fear conditioning with respect to both cue and context in individuals;

FIG. 7b shows context-induced fear responses measured by administering CORT to mice undergoing weak fear conditioning with respect to both cue and context in individuals;

FIG. 7c shows that LTD is not induced in the dorsal ITC of mice to which CORT is administered after fear conditioning;

FIG. 7d shows that context-induced fear response levels are increased after weak fearing conditioning subjected to cue in Dlx5/6-Cre (+) mice in which the D4R expression is inhibited in the dorsal ITC; and FIG. 7e shows the input-output curves for disynaptic IPSPs in the dorsal ITC.

DETAILED DESCRIPTION OF EXEMPLARY EMBODIMENTS

Figure 1A:
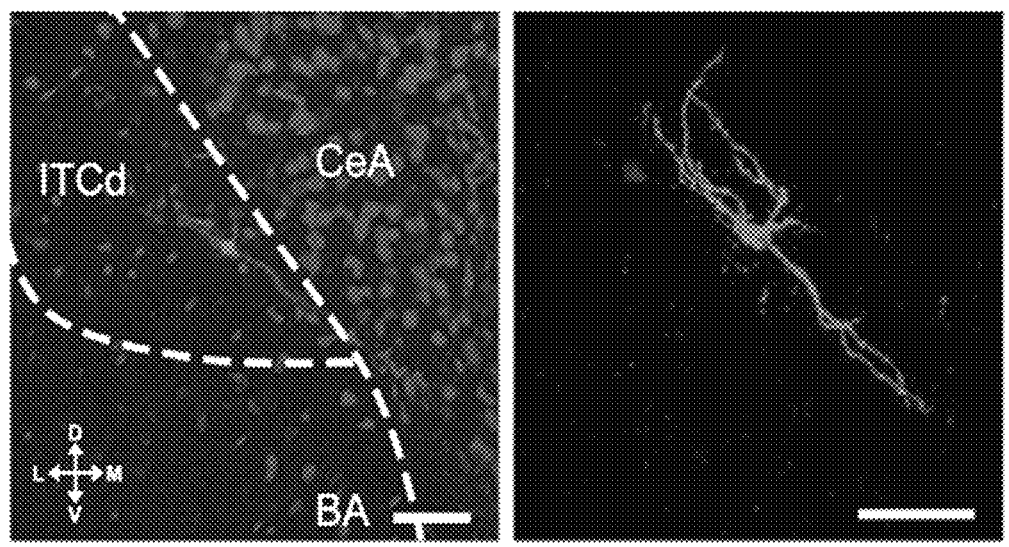

The amygdala of the brain is critical for expression of fear behavior and learning of stimuli associated with fear, and is known to store fear memories in neuronal circuits connected with the lateral nucleus and the central nucleus. However, since an inhibitory neuronal cell population regulating neuronal circuits has a small size (0.0098 mm$^3$ in mice), it is difficult to investigate and thus its role and regulatory mechanism have not been revealed.

In the present invention, the mechanism of operating the neuronal circuits inhibiting and regulating an amygdala region in which fear-associated stimulation occurs was investigated. Specifically, it was revealed that LTD easily takes place in an inhibitory cell population of weak fear-learned mice, and such synaptic plasticity is eliminated from the mice by an optogenetic method, resulting in excessive fear responses. Optogenetics is a systemic neuroscience technique for enabling on/off of activity of neurons by illumination of light with a specific wavelength range after genes responding to light have been artificially expressed in neurons.

In addition, in the present invention, it was confirmed that, even after weak fear conditioning, strong fear responses were exhibited from both of mice exhibiting PTSD and mice exhibiting inhibited D4R expression in the dorsal ITC.

Therefore, it was established that activation of a DA receptor by weak fear learning evokes LTD, thereby controlling strong fear behavior, but when PTSD occurs or the DA receptor is not properly functioning, LTD is not induced, which means that a neural transmission signal may not be weakened, and excessive fear responses are shown.

Specifically, in the present invention, synaptic plasticity in the dorsal ITC was assessed using the STDP stimulation protocol. STDP stimulation induced LTD in the lateral nucleus-dorsal ITC pathway of the amygdala after weak fear conditioning, but not after strong fear conditioning. Moreover, it was confirmed that induction of LTD in the dorsal ITC depends on activation of D4R and an increase in GABA release from neighboring ITC neurons. Particularly, it was confirmed that selective blockade or deficiency of D4R in the region of the amygdala centered on the dorsal ITC or optogenetic manipulation that reverses the LTD in the lateral nucleus-dorsal ITC pathway of the amygdala in vitro results in increased fear responses in mice, and therefore it can be seen that revealed that D4R-dependent LTD plays a critical role in the control of fear expression.

In addition, in the present invention, as a result of LTD analysis in a PTSD mouse model, LTD impairment was observed in the dorsal ITC. That is, through the present invention, it was confirmed that synaptic plasticity induced in the dorsal ITC is involved in controlling learned fear expression, and its impairment induces the occurrence of PTSD. These experimental results provide new insights into functional roles of a specific inhibitory circuit in the amygdala, which indicates that the range of emotional stimuli that can be retained as long-term memory can be distinguished.

As described above, in the present invention, not only the mechanism for fear memory expression by a dopamine receptor and LTD was revealed, but the association between PTSD and the inhibitory neuronal circuit in the amygdala was also revealed, which will significantly contribute to the development of a therapeutic agent for fear-related psychiatric diseases.

The present invention provides a PTSD animal model in which D4R is damaged or depleted in the dorsal ITC of the amygdala.

Dopamine (DA) is a neurotransmitter essential for neural signal transmission found in the brain of animals including humans, and a DA receptor is a 7-transmembrane (G protein-coupled) peptide that transmits a DA-linked signal into cells. In the present invention, it was confirmed that only subtype 4 (D4R) among DA receptor subtypes 1 to 5 (D1R to D5R) induces LTD in the dorsal ITC.

In the present invention, PTSD refers to a mental disease that can occur after mental trauma due to a severe accident, and has major symptoms such as hypersensitivity, re-experience of shocks, or emotional avoidance or numbness.

In the present invention, intercalated cell masses (ITCs) refer to a population of neurons regulating fear-related behavior by adjusting a signal between nuclei in the amygdala, and the dorsal ITC is located between the lateral nucleus and the central nucleus in the amygdala, and receives a glutamatergic signal from the lateral nucleus, and sends a GABAergic inhibitory signal to the central nucleus and the lateral region of the ventral ITC.

In the present invention, long-term depression (LTD) refers to a phenomenon in which signal transmission intensity of a synapse, which links neurons, is consistently weakened.

Also, the present invention provides a method for preparing a PTSD animal model in which D4R is impaired or depleted in the dorsal ITC of the amygdala.

In the present invention, knock-down or knock-out of a D4R gene may result in damage or depletion of a protein. Knock-down or knock-out methods are not limited, and may employ various known methods, for example, shRNA, siRNA, microRNA, antisense oligonucleotides, PNA, aptamers, and CRISPER Cas9 techniques, which target the gene.

Also, the present invention provides a method for screening a drug for preventing or treating PTSD using the animal model.

In the present invention, a material for activating D4R may be selected as a drug by treating a PTSD animal model with a candidate drug and measuring D4R activity in the amygdala.

In the present invention, an agonist capable of activating the D4R may be any material having activity similar to DA without limits, for example, one or more selected from the group consisting of materials listed below, such as N-([4-(2-cyanophenyl)piperazine-1-yl]methyl)-3-methylbenzamide (PD-168077).

PD 168077 maleate: N-(methyl-4-(2-cyanophenyl)piperazinyl-3-methylbenzamide maleate A 412997 dihydrochloride: N-(3-methylphenyl)-4-(2-pyridinyl)-1-piperidineacetamide ABT 724 trihydrochloride: 2-[[4-(2-pyridinyl)-1-piperazinyl]methyl]-1H-benzimidazole trihydrochloride WAY 100635 maleate: N-[2-[4-(2-methoxyphenyl)-1-piperazinyl]ethyl]-N-2-pyridinylcyclohexanecarboxamide maleate Ro 10-5824 dihydrochloride: 5-[(3,6-dihydro-4-phenyl-1(2H)-pyridinyl)methyl]-2-methyl-4-pyrimidinamine dihydrochloride Also, the present invention provides a pharmaceutical composition for preventing or treating PTSD, comprising a drug detected by the screening method as an active ingredient.

The term "pharmaceutical composition" used herein may further include a conventional therapeutic active ingredient, other adjuvants, pharmaceutically acceptable carriers, etc. The pharmaceutically acceptable carriers include a saline solution, sterilized water, Ringer's solution, a buffered saline, a dextrose solution, a maltodextrin solution, glycerol, and ethanol.

The composition may be used by being prepared in the form of oral preparations such as powder, granules, tablets, capsules, suspension, emulsion, syrup, aerosol, etc., external applications, suppositories and sterilized injections according to individual conventional methods.

The term "dose" used herein may vary according to a patient's body weight, age, sex, health condition, diet, the number of doses, an administration method, an excretion rate and severity of a disease, which is obvious to those of ordinary skill in the art.

The term "subject" used herein refers to a target needing treatment for a disease, and more specifically, a mammal such as a human or a non-human primate, a mouse, a rat, a dog, a cat, a horse or a cow.

The term "pharmaceutically effective amount" used herein may be determined by factors including a disease type, severity of a disease, a patient's age and sex, sensitivity to a drug, administration time, an administration route, an excretion rate, treatment duration, and a simultaneously used drug, and other factors well known in the medical field, and refers to an amount capable of obtaining the maximum effect without side effects, in consideration of all of the above factors, which may be easily determined by those of ordinary skill in the art.

The composition of the present invention is not limited to one administration method as long as it can reach target tissue. For example, the administration method includes oral administration, intraarterial injection, intravenous injection, transdermal injection, intranasal administration, transbronchial or intramuscular administration, etc. A daily dose may be approximately 0.0001 to 100 mg/kg, and preferably 0.001 to 10 mg/kg, which is preferably administered daily once to several times.

The D4R agonist of the present invention may induce LTD in the dorsal ITC of the amygdala, thereby inhibiting fear responses, and thus may be usefully applied in prevention or treatment of PTSD.

Hereinafter, examples will be provided to help in understanding the present invention. However, the following examples are merely provided to more easily understand the present invention, and the scope of the present invention is not limited to the examples.

EXAMPLES

Example 1: Materials & Methods 1-1. Animals

Male C57BL/6J, D4R-KO, and Dlx5/6-Cre and Ail4 reporter mice from Jackson Laboratory (Bar Harbor, Me.) were housed under a 12-hour light/dark cycle and given ad libitum access to food and water. All procedures for animal experiments were approved by the ethical review committee of POSTECH (Pohang University of Science & Technology), Korea and performed in accordance with the relevant guidelines.

1-2. Plasmid and Viral Vectors pCMV6-AC-D4R-turboGFP was purchased from OriGene Technologies (Rockville, Md.). shRNA sequences targeting D4R (gctgctcatcggcttggtgtt) were also obtained from OriGene Technologies and cloned into pLL3.7 construct. Then, the effectiveness of shD4R sequence was verified with quantitative RT-PCR using HEK-293 cells (GenTarget, San Diego, Calif.) co-transfected with pCMV6-AC-D4R-turboGFP and pLL3.7-shD4R. To achieve simultaneous Cre-dependent knock-down and eYFP expression in the same cells, pAAV-EF1α-DIO-eYFP, was modified by inserting U6 promoter and TATAlox and adding new sequences. The resultant plasmids, cKDeYFP-shD4R (pAAV-EF1α-DIO-TATAlox-eYFP-U6-shD4R) and control cKD-eYFP (pAAV-EF1α-DIO-TATAlox-eYFP-U6) vectors were used for production of the corresponding viruses.

Virus production was conducted in accordance with established protocols. Briefly, HEK-293 cells were co-transfected with helper plasmids and either cKD-eYFPshD4R or cKD-eYFP at an equal molar ratio using Lipofector-Q transfection reagents (AptaBio, Korea). 72 hours after co-transfection, the cells were lysed through freeze-thaw steps and resultant AAV particles were purified by iodixanol-gradient ultracentrifugation at 340,000 g for 2 hours. AAV particles were concentrated with Amicon Filter (100K, Millipore, Bedford, Mass.) to achieve at least $5.0 \times 10^{12}$ gc/ml.

1-3. Western Blot

Normal HEK-293 and Cre-expressing HEK-293 were cultured in Dulbecco's modified Eagle's medium (DMEM) supplemented with 10% fetal bovine serum (Hyclone, South Logan, Utah) and 100 U/ml penicillin and 100 g/ml streptomycin. They were incubated at 37° C./5% CO2.

For heterologous expression of D4R, we transfected HEK-293 cells with pCMV-D4R-turboGFP using Lipofector-Q. D4R-transfected cells were further treated with either rAAV2-cKD-eYFP or rAAV2-cKD-eYFP-shD4R. 2 days after viral infection, total proteins were extracted using HEPES lysis buffer (40 μM HEPES, 120 mM NaCl, 1 mM EDTA, 1% Triton X-100) containing protease inhibitor cocktail (Roche, Indianapolis, Ind.), separated on 10% SDS PAGE gel and then transferred onto PVDF membrane (0.45 μm pore, Millipore).

The membranes were blocked for 1 hour in TBST (Tris-buffered-saline and Tween 20) containing 5% skim milk and then individually incubated overnight at 4° C. with anti-D4R (sc-31481, 1:1000, Santa Cruz, Paso Robles, Calif.), anti-GFP (LF-PA0043, 1:1000, AbFrontier, Korea) or anti-GAPDH (sc-25778, 1:1000, Santa Cruz) antibodies. HRP-conjugated anti-goat (sc-2020, 1:5000, Santa Cruz) or anti-rabbit (A120-201P, 1:5000, Bethyl Laboratories, Montagomery, Tex.) antibodies were applied as secondary antibodies and treated at room temperature (RT) for 1 hour. Western blots were visualized with ECL reagent (WB-KLS0100, Millipore) and scanned with LAS-4000 (GE Heath Care, Piscataway, N.J.). Quantitative analysis was performed with ImageJ (NIH, Bethesda, Md.).

1-4. Immunocytochemistry

HEK-293 cells were plated onto 12-mm glass coverslips coated with 0.1 mg/ml poly-L-lysine and then treated with either rAAV2-cKD-eYFP-shD4R or rAAV2-cKD-eYFP. Following 3 days-incubation, the coverslips were fixed with a fixative solution containing 4% paraformaldehyde in phosphate buffered saline (PBS) at 4° C. for 24 hours and permeabilized with 0.25% Triton X-100 in PBS at 25° C. for 10 minutes. Then the samples were blocked with 1% BSA, 5% normal goat serum and 0.25% Triton X-100 in PBS.

For Cre staining, anti-Cre (MAB3120, 1:500, Millipore) antibody was applied at 4° C. for 12 hours and then goat antimouse Alexa Fluor 568 conjugated IgG (A11004, 1:500, Invitrogen, Carlsbad, Calif.) antibody at RT for 1 hour. The samples were mounted on glass slides with mounting medium (Santa Cruz) containing DAPI.

1-5. Immunohistochemistry

Mice were deeply anesthetized with tribromoethanol (250 mg/kg) and transcardially perfused with PBS and then a fixative solution (4% paraformaldehyde in PBS). The isolated brains were kept in the fixative solution for overnight at 4° C. The brains were embedded in 5% agarose and sliced into 50-μm thick coronal sections with a vibratome (VT1000S, Leica, Germany). Sliced sections were blocked with 4% normal donkey serum and 0.4% Triton X-100 in PBS at 4° C. for 1 hour and then were incubated with goat anti-D4R (sc-31481; 1:500, Santa Cruz), rabbit anti-synaptophysin (04-1019; 1:1000, Millipore) or mouse anti-gephyrin (sc-25311, 1:300, Santa Cruz) antibodies at 4° C. overnight. Donkey anti-goat DyLight 488 conjugated IgG (1:300, Bethyl Laboratories) or donkey anti-goat Alexa Fluor 594 conjugated IgG (1:300, Invitrogen), donkey anti-rabbit Alexa Fluor 568 conjugated IgG (1:300, Invitrogen) or DyLight 550 conjugated donkey anti-mouse IgG (1:300, Bethyl Laboratories) antibodies were used as secondary antibodies.

For c-Fos staining, we used rabbit anti-c-Fos (sc-52, 1:500, Santa Cruz) as primary antibody and goat anti-rabbit Alexa Fluor 647 conjugated IgG (1:500, Invitrogen) as secondary antibody after blocking with 4% normal goat serum in PBS. All tissues were mounted on the slide glasses with UltraCruz mounting medium (Santa Cruz).

1-6. Cellular Imaging

We used laser scanning confocal microscopes (LSM 510, Zeiss, Germany or Fluoview 1000, Olympus, Japan) for cellular imaging experiments except for co-localization between D4R and synaptic marker proteins. We also used a structured illumination microscope (N-SIM, Nikon, Japan) to examine co-localization of D4R and gephyrin/synaptophysin further precisely rather than conventional confocal microscopy. Quantitative analysis of immunoreactive puncta was performed using MetaMorph 7.7 software (Molecular Devices, Sunnyvale, Calif.).

1-7. Post-Embedding Immuno-Gold Electron Microscopy

Immuno-EM was conducted in accordance with established protocols. Transcardial perfusion and preparation of brain slices were identical to those used for the immunohistochemistry experiments except thickness of slices being 200 μm. The dorsal ITC areas were isolated from the amygdala slices under a dissection microscope (Olympus). The tissue was immersed into a 0.001% osmium tetroxide (OsO4) solution on the ice for 1 hour to achieve the membrane preservation and then rinsed with PBS. Then, the tissue was kept in a 10% sucrose solution for cryoprotection. High-pressure freezing system (HPM 100, Leica) was used to acutely freeze the tissue while preserving the membrane and cellular components. After acute freezing, sample tissue was kept in acetone and embedded in Lowicryl HM20 resin (Electron microscopy sciences, Hatfield, Pa.) at −45° C. for 2 days and UVpolymerization for 1 day with EM AFS2 (Leica). UV-polymerized blocks containing the dorsal ITC tissues were sliced by an ultra-microtome (Leica). These slices were then put on the Nickel grids (FCF200-Ni, Electron microscopy sciences).

For immunostaining, goat anti-D4R (1:20, Millipore) and mouse monoclonal anti-GAD67 (MAB5406, 1:20, Millipore) antibodies were used as primary antibodies. Subsequently, 12-nm gold particle-Donkey anti-goat or 6-nm gold particle-Donkey anti-mouse (705-205-147 and 715-195-150, respectively, Jackson Immuno Research, West Grove, Pa.) antibodies were used for labeling D4R or GAD-67, respectively after blocking with 0.2% normal donkey serum in detergent-free PBS at 4° C. overnight. After antibody application, we treated 1-2% uranyl acetate for 4 minutes and Reynolds solution for 2 minutes to obtain a high-contrast image. Images were obtained with a transmission electron microscope (JEM-1011, Jeol, Japan).

1-8. Virus Infusion and Implantation of Tungsten Electrodes and Optic Fibers

After mice were anesthetized with ketamine and xylazine, the head was fixed in a stereotaxic frame (Kopf, Tujunga, Calif.). For viral infusion, ~0.1 μl of virus solution was infused using horizontally pulled glass needles, into each hemisphere with Nanoject II (Drummond scientific instrument, Broomall, Pa.) for 1 minute (4 injections per hemisphere were applied, 23.0 nl per injection which had a rate of 46 nl/sec), and the injection needles remained for additional 10 minutes to allow diffusion of AAV.

Single tungsten electrodes were ipsilaterally implanted to reach the dorsal ITC for recording in vivo activity and IL for in vivo stimulation in the aforementioned coordinates, and secured with screws and dental cement. To ensure the recording electrodes were placed correctly in the dorsal ITC, we electrically stimulated IL (0.1 Hz) while neural activity was monitored from the dorsal ITC. If burst-like spikes were observed earlier than 50 ms from each IL stimulation, the recording electrodes were secured with dental cement. Optic fibers (50-μm core diameter, ThorLabs, Newton, N.J.) were secured to a multi-mode zirconia ceramic ferrule (Precision Fiber Products, Milpitas, Calif.) with adhesive and epoxy, and then implanted to place its tip on the dorsal atop of the dorsal ITC in the coordinate, AP−1.4 mm, ML±3.2 mm, DV−4.0 mm from the bregma, and secured with dental cement.

1-9. Drug Infusion

Guide cannulae were implanted bilaterally (26 gauge, Plastics One, Roanoke, Va.) aimed into the dorsal ITC areas in the coordinates, AP−1.4 mm, ML±3.2 mm, DV−4.2 mm from the bregma, and were fixed in the skull with dental cement. The cannulae remained capped with internal dummy cannulae (33 gauges, Plastics One) after surgery. Animals were individually housed and allowed to recover at least for 1 week after surgery. The mice bilaterally received 0.5 μl of either L-745870 or vehicle through the injection cannula (33 gauge, Plastics One) connected to a 10-μl Hamilton syringe for 5 minutes at a rate of 0.1 μl/min using microinfusion pump (Harvard Apparatus, Holliston, Mass.) 20 minutes before fear conditioning. L-745870 was dissolved to 500 nM in 0.9% saline just before the infusion. Mice were kept with injector cannulae for additional 5 minutes after the end of infusion and then were subjected to fear conditioning. To estimate the diffusion range of L-745870, FITC (500 nM) was also included in the injectant for certain experiments. The subject mice were transcardially perfused right after the last behavioral tests and analyzed for the injection loci. Data from the animals with wrong placement of cannula tips were excluded from further analyses.

1-10. Behavioral Tests

We used two different chambers (26 cm×26 cm×24 cm). Context A consisted of black opaque PVC walls and a grid floor, which was swiped with 70% ethanol before each trial whereas context B consisted of transparent plastic walls and a PVC floor covered with cage bedding and was scented with peppermint odor.

Fear conditioning trainings were conducted in context A within sound-attenuating conditions (Panlab, Spain). Tone CS (conditioned stimulus) was delivered with a speaker while electric foot shock US (unconditioned stimulus) was applied through a floor grid attached to a shock generator (Panlab). The chambers were also equipped with infrared webcams connected to a personal computer to store animal behavior. Mice were placed in the context A for 2 minutes of acclimation and were then presented with auditory tone (CS: 3 kHz, 80 dB for 30 sec) that were co-terminated with electric foot shocks (US: 0.4 or 0.8 mA for 0.5 sec). Total 8 CS-US pairs were presented in pseudorandom intertrial intervals (varied from 60 to 120 sec). 24 hours after fear conditioning, mice were placed in context B to assess the recall of fear memory by being re-exposed to CS, but without US for 2 minutes.

To induce PTSD-like memory impairment, corticosterone (CORT, 5 mg/kg) or vehicle (saline, 0.9% NaCl) was intraperitoneally (i.p.) injected immediately after fear conditioning as previously described. The cue-conditioning group underwent weak fear conditioning with the previously-described CS-US pairing paradigm in context A and was tested for fear recall toward the cue in context B at the next day.

To assess contextual fear memory from cue conditioned animals, the mice were placed again in context A 2 hours after termination of the first recall test and then duration of freezing was measured for 2 minutes without presentation of the auditory cue. The mice were placed in context B 2 hours after termination of the first recall test and the freezing time during presentation of the auditory cue was measured for 2 minutes.

The D4 agonist (PD 168077, Tocris, 1 mg/kg) or Vehicle was intraperitoneally (i.p.) injected 15 min only before the context A exposure.

1-11. ChR2-Mediated Optical Stimulation rAAV5-CamKIIα-hChR2(H134R)-eYFP and rAAV5-CamKIIα-eYFP from Vector Core of University of North Carolina were used for optogenetic manipulation. Optical activation of axon terminals of the dorsal ITC neurons for STDP induction was performed by illuminating acute slices with 1-msec blue light pulses from LED source (ThorLabs). The light intensity was adjusted to evoke robust EPSPs. 473-nm DPSS blue laser (Shanghai Laser & Optics Century, China) was utilized to apply in vivo optogenetic TBS to the LA-dorsal ITC pathway. The optogenetic TBS was delivered through a custom-made patch cable (50-μm core diameter fiber optics, ThorLabs). This TBS was composed of 10 sets of light pulses at 0.1 Hz, each set of 10 pulse trains at 5 Hz, and a single train had 4 light pulses at 50 Hz. The generation of optogenetic TBS was controlled by Master-8 stimulator (AMPI, Israel). During optogenetic TBS, the mice were allowed to freely move nearby their home cage without any anesthetization. The putative light loss was carefully compensated for attenuation through the implanted part, which was measured prior to the surgery. Geometric light loss in the brain was also predicted and compensated with the web-based light transmission calculator (http://optogenetic.org/). After transcardial perfusion, we validated that each optic fiber withdrawn from the skull did not exhibit a significant difference in light loss from the measurement prior to the surgery.

1-12. Slice Electrophysiology

Acute brain slices were placed in recording chambers and continuously superfused (2 ml/min) with a bathing solution containing 119 mM NaCl, 2.5 mM KCl, 2.5 mM CaCl2, 2 mM MgSO4, 1.25 mM NaH2PO4, 26 mM NaHCO3, and 10 mM D-glucose while equilibrated with 95% O2 and 5% CO2 (pH 7.3-7.4) at RT. Whole-cell patch recordings in current clamp mode or voltage clamp mode were made with a MultiClamp 700B amplifier (Molecular Devices). Recording electrodes (8-10 M) were filled with an internal solution containing, for EPSP recordings: 120 mM K-gluconate, 5 mM NaCl, 1 mM MgCl2, 0.2 mM EGTA, 10 mM HEPES, 2 mM MgATP, and 0.1 mM NaGTP at pH 7.2 adjusted with KOH, for EPSC recordings: 130 mM CsMeSO4, 8 mM NaCl, 0.5 mM EGTA, 10 mM HEPES, 2 mM MgATP, 0.1 mM NaGTP, 5 mM QX-314, 10 mM phosphocreatine at pH 7.2 adjusted with CsOH, for IPSP recordings: 135 mM KCl, 10 mM NaCl, 2 mM MgCl2, 0.5 mM EGTA, 10 mM HEPES, 2 mM MgATP, 0.1 mM NaGTP at pH 7.2 adjusted with KOH, and for IPSC recordings: 135 mM CsCl, 1 mM EGTA, 10 mM HEPES, 2 mM MgATP, 0.1 mM NaGTP, and 5 mM QX-314 at pH 7.2 adjusted with CsOH.

To compare mPSCs without or after STDP, KCl-based and K-gluconate-based internal solutions were used for recording mIPSCs and mEPSCs, respectively. K-gluconate based solution was also used to record EPSCs and IPSCs evoked by interleaved stimulation. Series resistance (10-30 MΩ) was monitored throughout all experiments. mEPSCs were recorded at −70 mV holding potential in the presence of 1 μM tetrodotoxin (TTX) and 100 μM picrotoxin (Tocris, UK) while mIPSCs were measured at −70 mV in the presence of 1 μM TTX, 25 μM NBQX, and 50 μM 2-amino-5-phosphonovaleric acid (APV, Tocris). Miniature PSCs were analyzed with MiniAnalysis (Synaptosoft, Fort Lee, N.J.) or Clampfit 10.1 software (Molecular Devices). For PSC recordings with interleaved stimulation, the holding potential was briefly (~40 ms) changed from −70 mV to +10 mV to reach the reversal potential of EPSC for isolation of putative IPSCs. For STDP experiments, stimulus intensity was adjusted to elicit EPSPs displaying 25%-30% of the maximum amplitudes. After obtaining stable baseline recording, 80 presynaptic stimuli were delivered at 2 Hz via metal stimulating electrode placed in LA while paired with action potentials induced by injection of depolarizing current to postsynaptic neurons. Quantal contents were estimated by obtaining the inverse square of the coefficient of variation ($1/CV^2$). Each $1/CV^2$ value was measured and calculated from 50 EPSCs or 50 IPSCs as previously described.

GDPβS (0.5 mM) was included in the internal solution to examine the presynaptic/postsynaptic contribution of D4R-mediated signaling to DA-LTD. Liquid junction potential between K-gluconate based internal solution and extracellular ACSF (13.3 mV) was corrected for the representation of resting membrane potential. For a subset of neurons, neurobiotin (0.5%, Vector Labs, CA) was included in pipette solution for morphological characterization. There was no significant difference between the electrophysiological data from the neurons recorded with or without neurobiotin, and thus those data were combined. The neurobiotin-injected neurons were visualized by staining with Texas Red conjugated avidin (Vector Labs) after overnight fixation.

1-13. In Vivo Electrophysiology

Electrode-implanted mice were weakly anesthetized with ketamine and xylazine for the stable recording of spontaneous firings of the dorsal ITC neurons. Spontaneous firings were recorded 1 hour after the habituation session (before fear conditioning). Weak fear conditioning was conducted at 24 hours after the first in vivo recording. 24 hours after fear conditioning, spontaneous firings were recorded in the same manner (after fear conditioning). Signals from recording electrodes were amplified $10^4$ times and band-pass filtered between 10 kHz (lowpass) and 300 Hz (high-pass) with DAM80 differential amplifier (World Precision Instruments, Sarasota, Fla.), and digitized at 40 kHz using PowerLab/4sp (ADinstruments, Colorado Springs, Colo.). Spontaneous firings were further processed and monitored with Chart acquisition software (ADinstruments). Single units were sorted using Spike2 software (Cambridge Electronic Design, UK), as previously described. A single spike was initially detected by an amplitude threshold. All detected spike traces were isolated by comparing with template waveforms. If not matched with any existing templates, a new template waveform was created based on the waveform of the detected spike. The spike isolation was refined by principle component analysis. Units showing inter-spike interval less than 1 ms were discarded from further analysis. Total spike numbers from each unit were used to calculate the spontaneous firing frequency of the dorsal ITC neuron. The electrode placements were thoroughly ascertained via post mortem examination.

Example 2: Results 2-1. LTD Induction in the Dorsal ITC Synapses after Weak Fear Conditioning The dorsal ITC receives glutamatergic inputs from the LA and the medial prefrontal cortex (mPFC), which adjust fear responses. We have identified the dorsal ITC neurons spatially and morphologically (FIG. 1A).

Figure 1B:
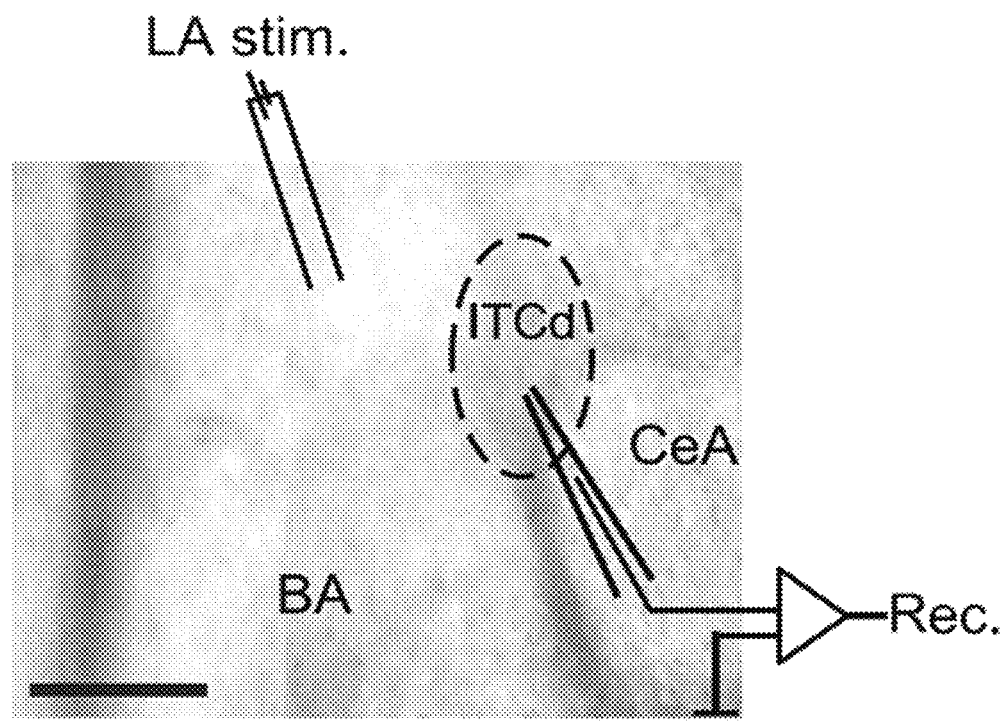

To assess synaptic properties in the LA dorsal ITC pathway and other neuronal features, we obtained whole-cell patch recordings of excitatory postsynaptic potentials (EPSPs) while stimulating LA (FIG. 1B) and induced STDP by applying 80 pairs of presynaptic stimulations and postsynaptic action potentials with various time intervals from EPSP initiation.

Interestingly, long-term potentiation (LTP) arose at +4- and +6-ms interval delays in the presence of the GABAA receptor antagonist picrotoxin, but not in the absence of picrotoxin. These data suggest that GABAergic transmission tightly regulates STDP in the dorsal ITC neurons as in the BLA neurons.

To analyze the behavioral and physiological consequences of different fear-conditioning protocols, we carried out Pavlovian fear conditioning by pairing a tone with either a sub-threshold (0.4 mA for 0.5 s, weak fear conditioning) or a supra-threshold US (0.8 mA for 0.5 s, strong fear conditioning).

Weak fear conditioning resulted in reduced levels of freezing at 24 hr after acquisition, which further decayed over the course of several days, comparable to those of the unpaired CS-US or the tone-only control groups. In contrast, strong fear conditioning led to significantly greater levels of freezing that remained elevated throughout the same time period (FIG. S1B). Thus, the weak fear conditioning seems to entail less-salient experience that could not be retained as long-lasting memory.

Figure 1C:
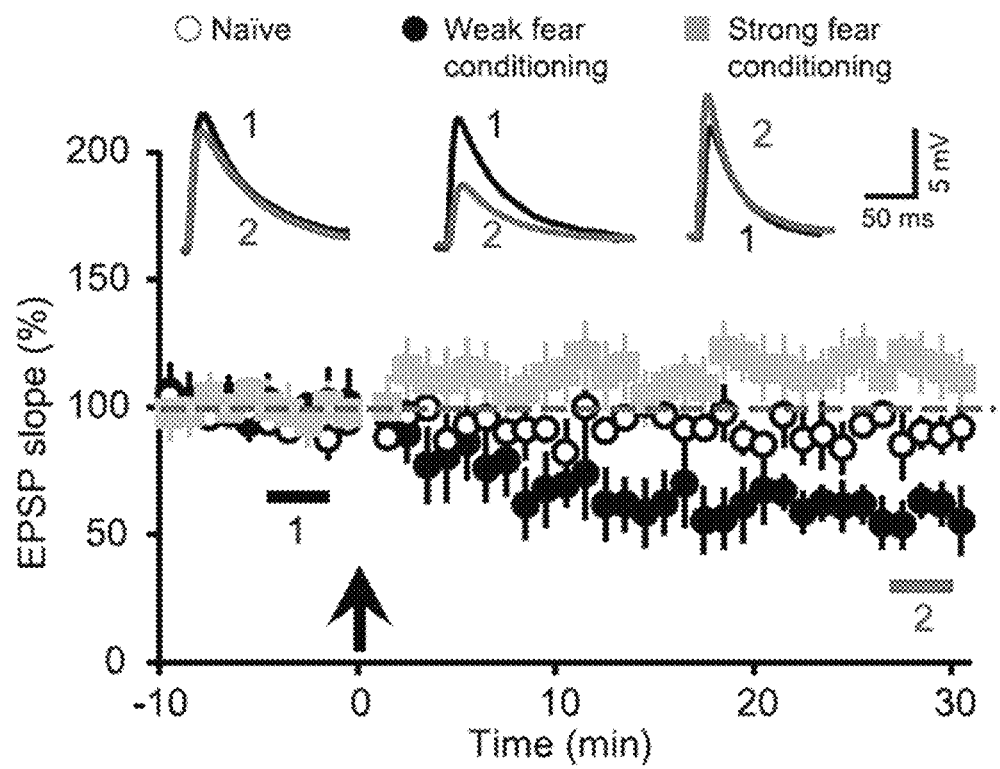

Importantly, LTD was induced in the dorsal ITC neurons by the same STDP protocol in the absence of picrotoxin (+6-ms interval at which GABAergic regulation was maximally effective for the induction of synaptic plasticity) in the amygdala slices prepared 24 hr after weak fear conditioning. However, we failed to detect any significant synaptic plasticity in slices from the animals that had undergone either strong fear conditioning or no training (naive) (FIG. 1C).

Figure 1D:
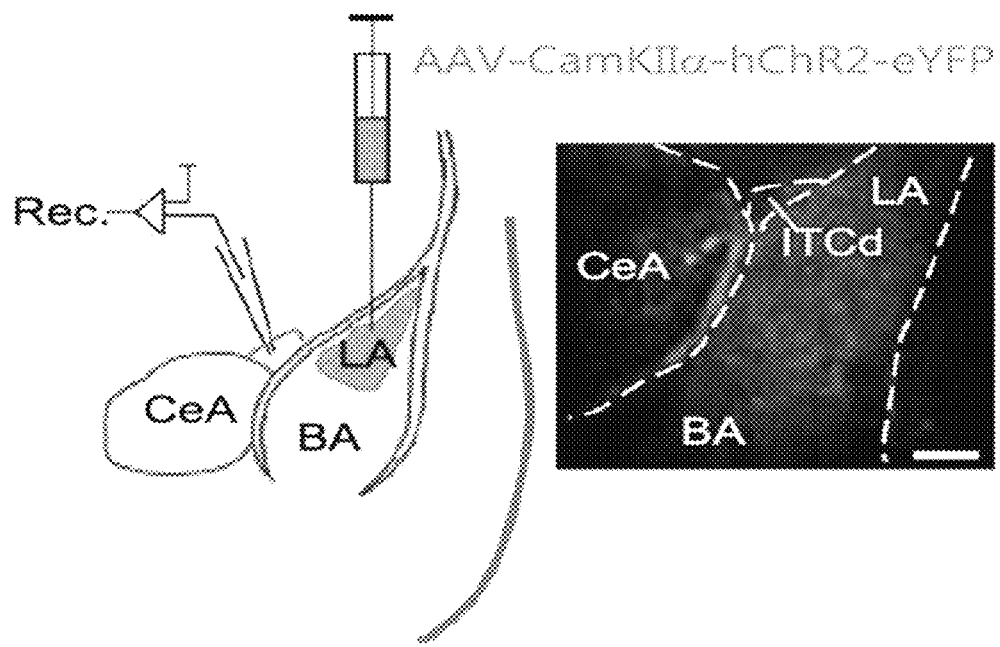

Although we elicited the synaptic responses in the dorsal ITC neurons by stimulation of LA, the possible existence of enpassant synapses projecting from the mPFC might have obscured which pathway expressed LTD. To further assess synaptic plasticity in distinct pathways, we infused adeno-associated virus (AAV) encoding channel rhodopsin-2 and enhanced yellow fluorescence protein (eYFP) into the LA or mPFC and then validated ChR2 expression with least retrograde infection (FIG. 1D).

Figure 1E:
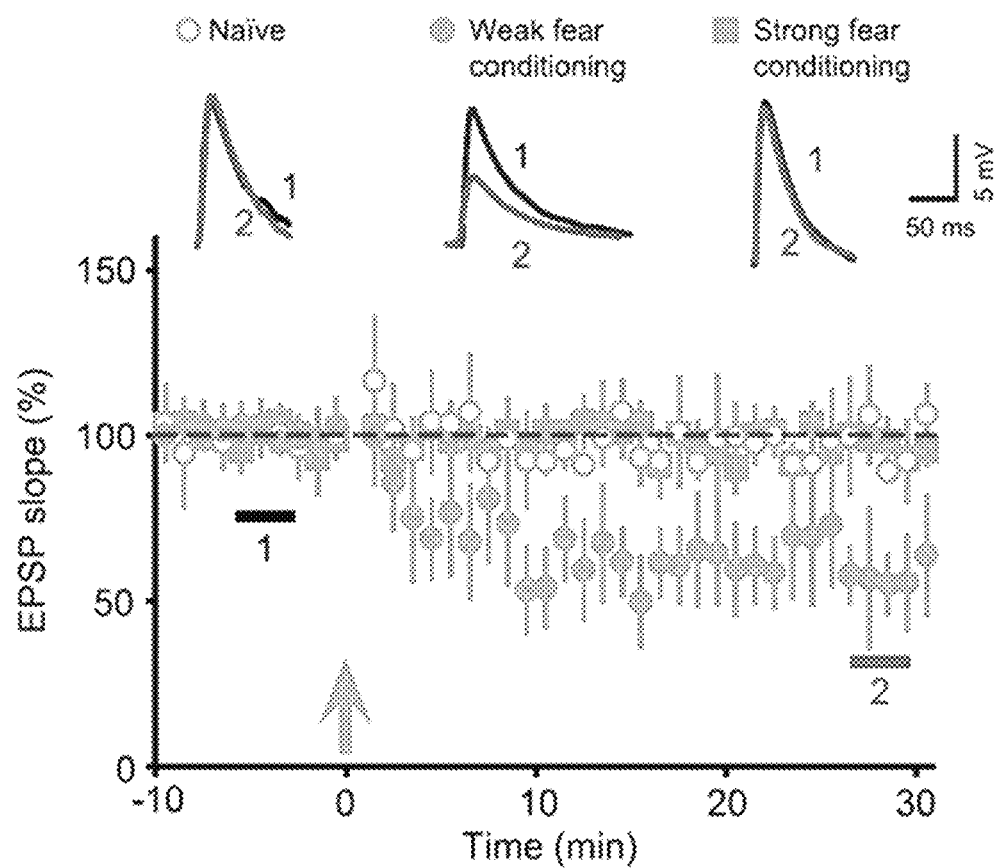

After the monosynaptic nature of optogenetically induced EPSPs was verified, we applied STDP-like optical stimuli. LTD was readily induced by the repeated pairing of light-elicited EPSPs and action potentials after weak fear conditioning when rAAV5-CamKIIa-hChR2-eYFP was infused into LA, but not when it was infused into the mPFC. The optical STDP also produced no synaptic plasticity in the amygdala slices prepared from naive animals or animals that underwent strong fear conditioning (FIG. 1E).

Therefore, LTD was induced at the synaptic connections from the LA to the dorsal ITC after weak fear conditioning.

2-2. Increased Inhibition to Dorsal ITC Neurons after Weak Fear Conditioning

Figure 2A:
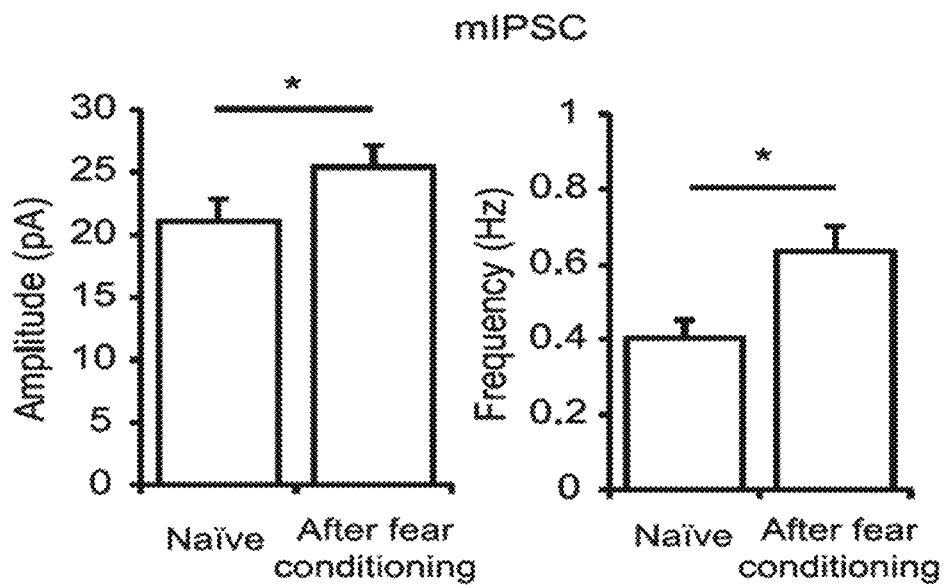
Figure 2B:
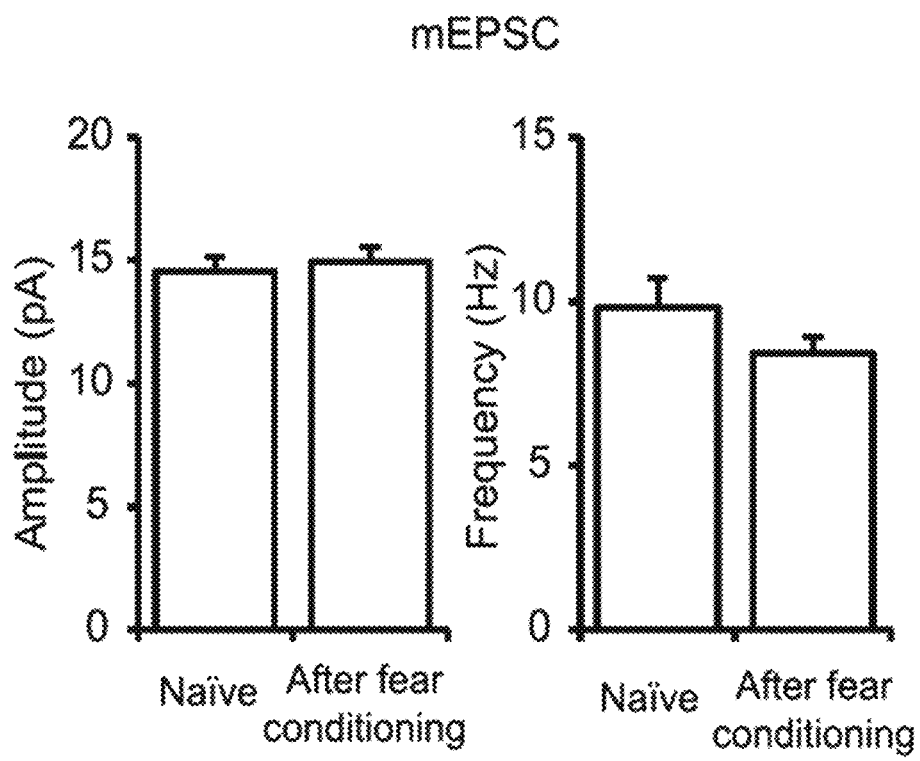

We monitored basal synaptic transmission and found that miniature IPSCs (mIPSCs) significantly increased after weak fear conditioning (FIG. 2A), whereas no significant change in miniature EPSCs (mEPSCs) was observed despite apparent reduction of excitatory transmission (FIG. 2B).

We also evoked disynaptic inhibitory postsynaptic potentials (IPSPs) in dorsal ITC neurons, because they receive GABAergic inputs from neighboring ITC neurons and glutamatergic inputs from the LA.

Figure 2C:
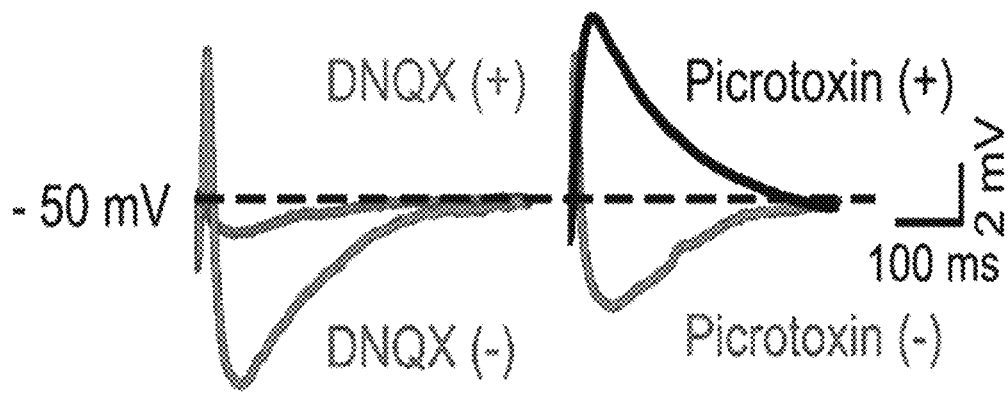
Figure 2D:
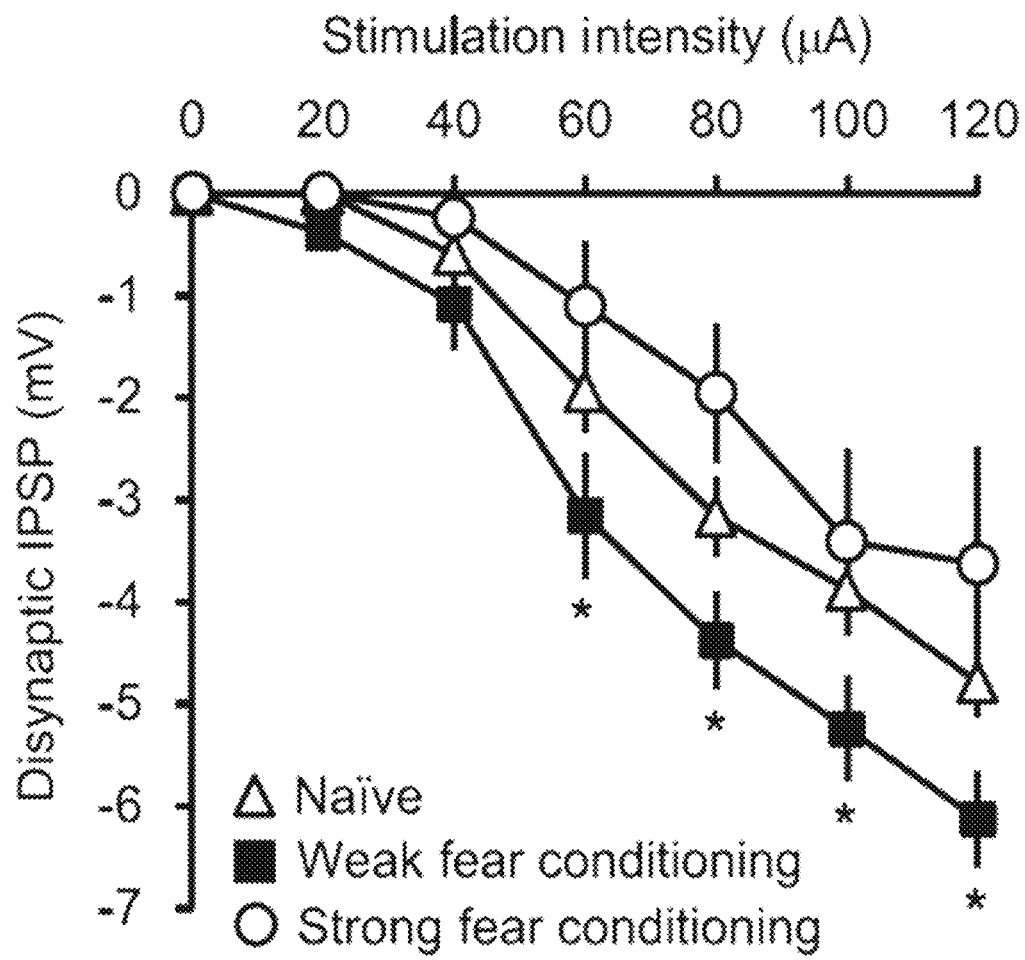

We observed biphasic PSPs, which consist of fast EPSP and slow IPSP, evoked by LA stimulation and confirmed the disynaptic nature by applying DNQX, an antagonist for a-amino-3-hydroxy-5-methyl-4-isoxazolepropionic acid (AMPA) and kainate receptors (FIG. 2C). The input-output curves revealed that the inhibitory drives to the dorsal ITC neurons significantly increased after weak fear conditioning compared with those in other groups (FIG. 2D). Thus, GABAergic inputs onto the dorsal ITC neurons might become enhanced by weak fear conditioning and thereby may contribute to the induction of LTD by shunting inhibition.

To examine whether neuronal activity of the dorsal ITC could be upregulated, we attempted to analyze the spontaneous activity in vivo before and after weak fear conditioning. To this end, we carefully defined the dorsal ITC neurons with their responses to electrical stimulation of the infralimbic regions of the mPFC of live animals and then confirmed the recording sites within the dorsal ITC through postmortem examination. However, we failed to detect significant changes in single-unit activity of those identified ITC neurons, suggesting that neuronal activity of the dorsal ITC itself was not significantly affected by weak fear conditioning.

2-3. DA-Dependent LTD by Activation of D4R

Figure 3A:
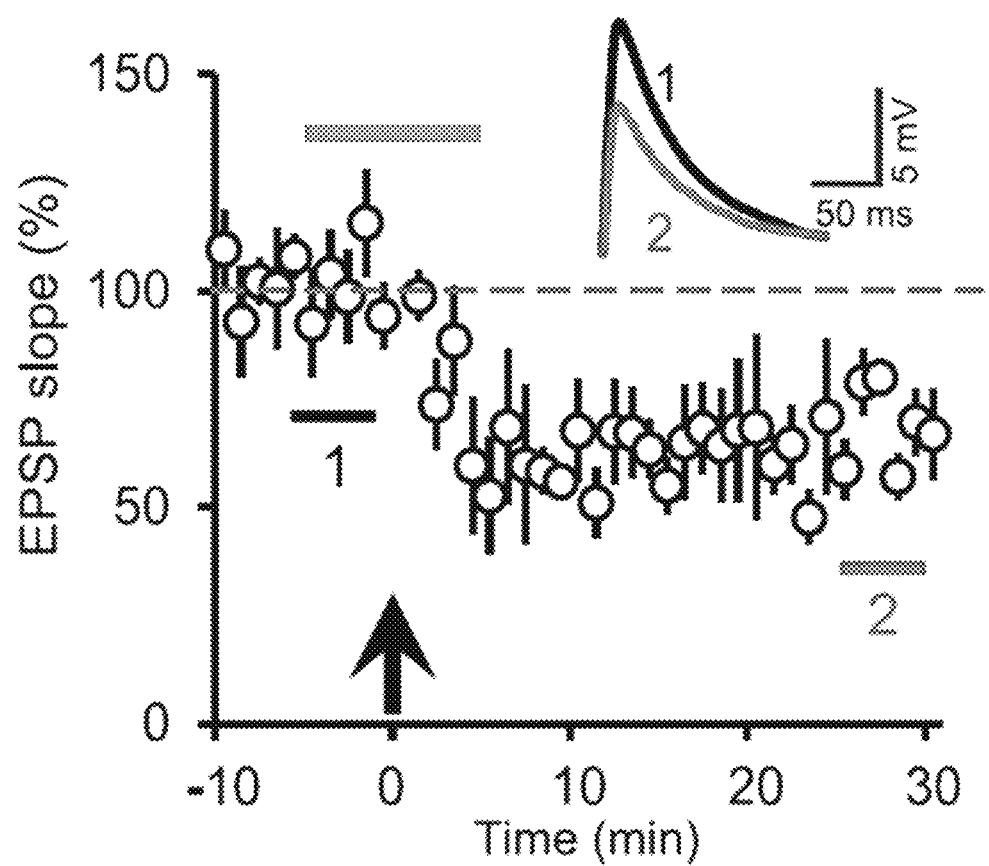

To address possible roles of DA in the dorsal ITC neurons, we analyzed their intrinsic properties in the presence of DA (30 mM) and detected only negligible changes in the resting membrane potentials (RMPs) and excitability before and after DA application. While bath application of DA alone did not alter synaptic transmission, LTD was readily induced by the STDP protocol in the presence of DA (30 mM) (FIG. 3A).

Figure 3B:
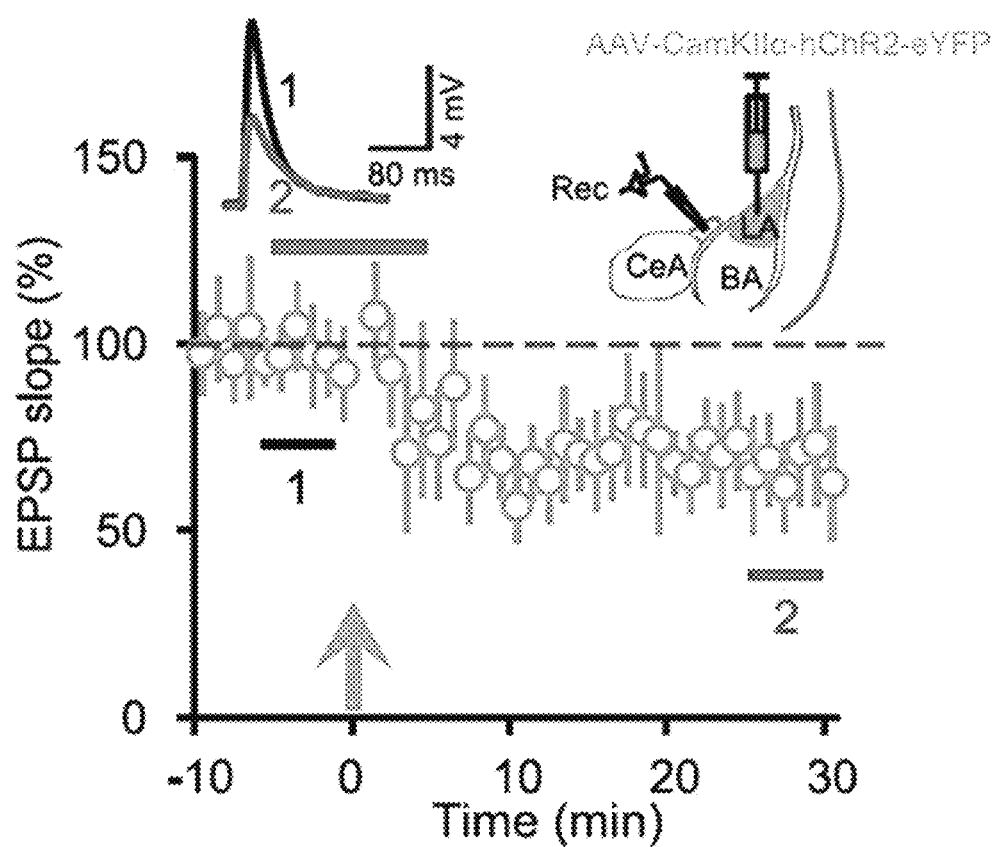

To specify the pathway expressing DA-dependent LTD (DA-LTD), we infused rAAV5-CamKIIa-hChR2-eYFP into LA and then were able to induce DA-LTD with photostimulation (FIG. 3B). These results support the idea that DA enables the synapses between the LA and dorsal ITC to undergo LTD, which is similar to what we had observed with LTD after weak fear conditioning.

Figure 3C:
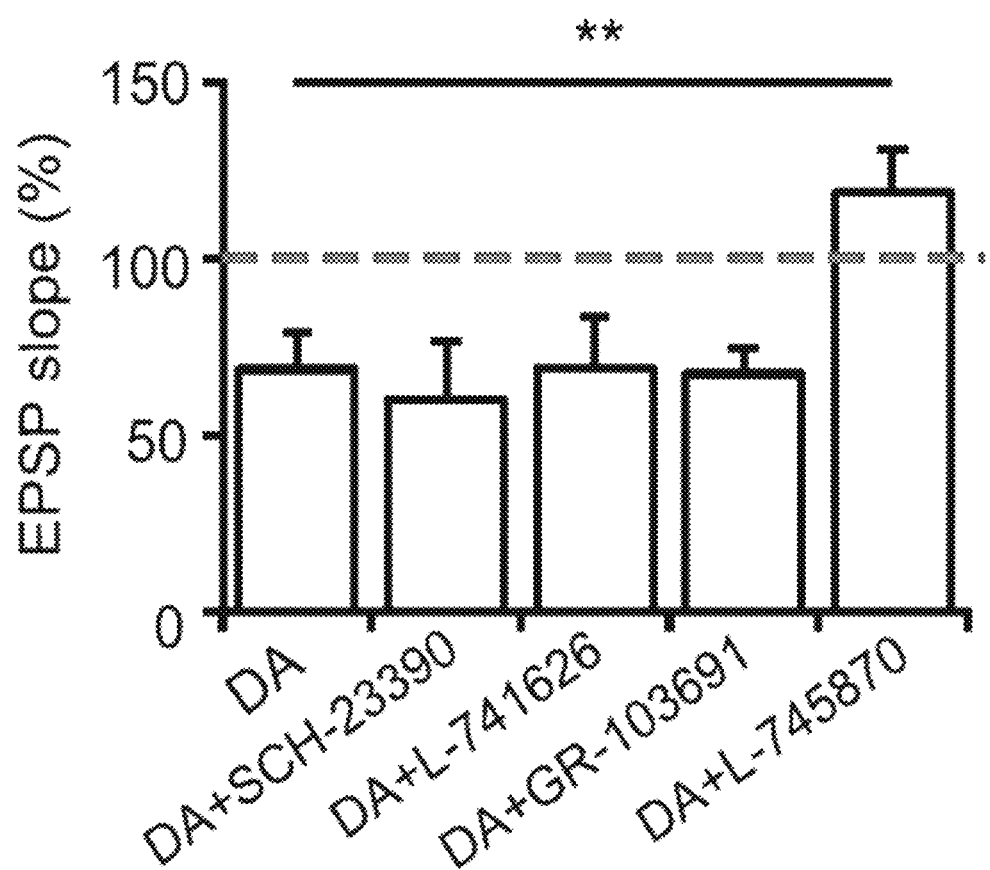

To identify which subtype of DA receptors plays a dominant role in the induction of DA-LTD, we blocked individual DA receptors with various antagonists in optimal concentrations selective for each receptor. Only a D4R-specific antagonist (L-745870) abolished DA-LTD, whereas antagonists of D1/5R (SCH-23390), D2R (L-741626), or D3R (GR-103691) did not affect DA-LTD (FIG. 3C).

Figure 3D:
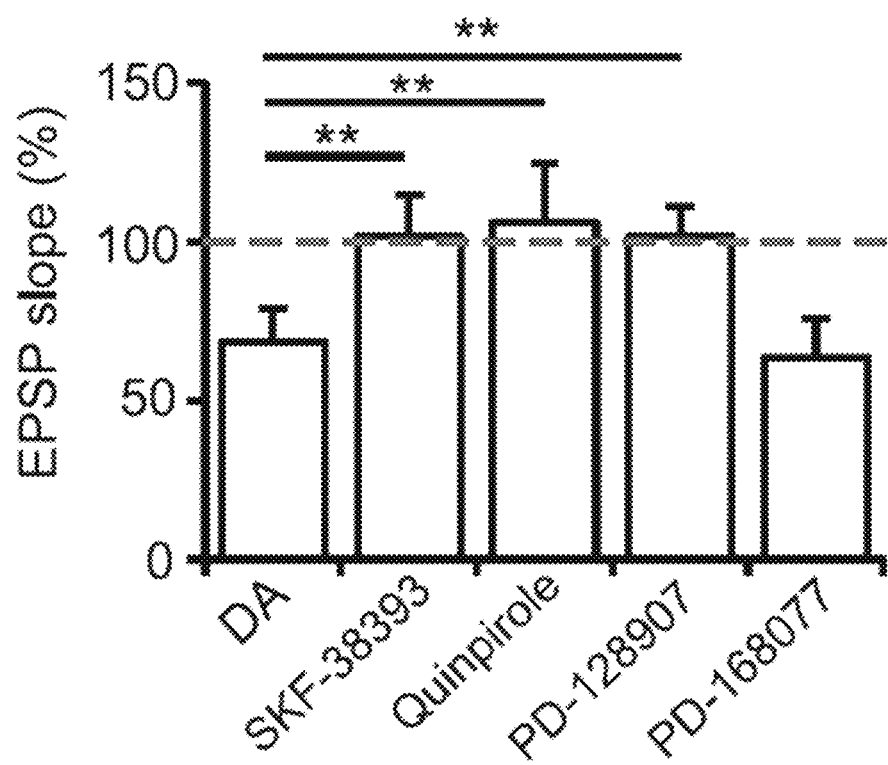

Consistent with the antagonist data, activation of D4R with PD-168077 allowed for the induction of LTD at the dorsal ITC as effectively as DA did, but the agonists for D1/5R (SKF-38393), D2R (quinpirole), or D3R (PD-128907) did not (FIG. 3D).

Figure 3E:
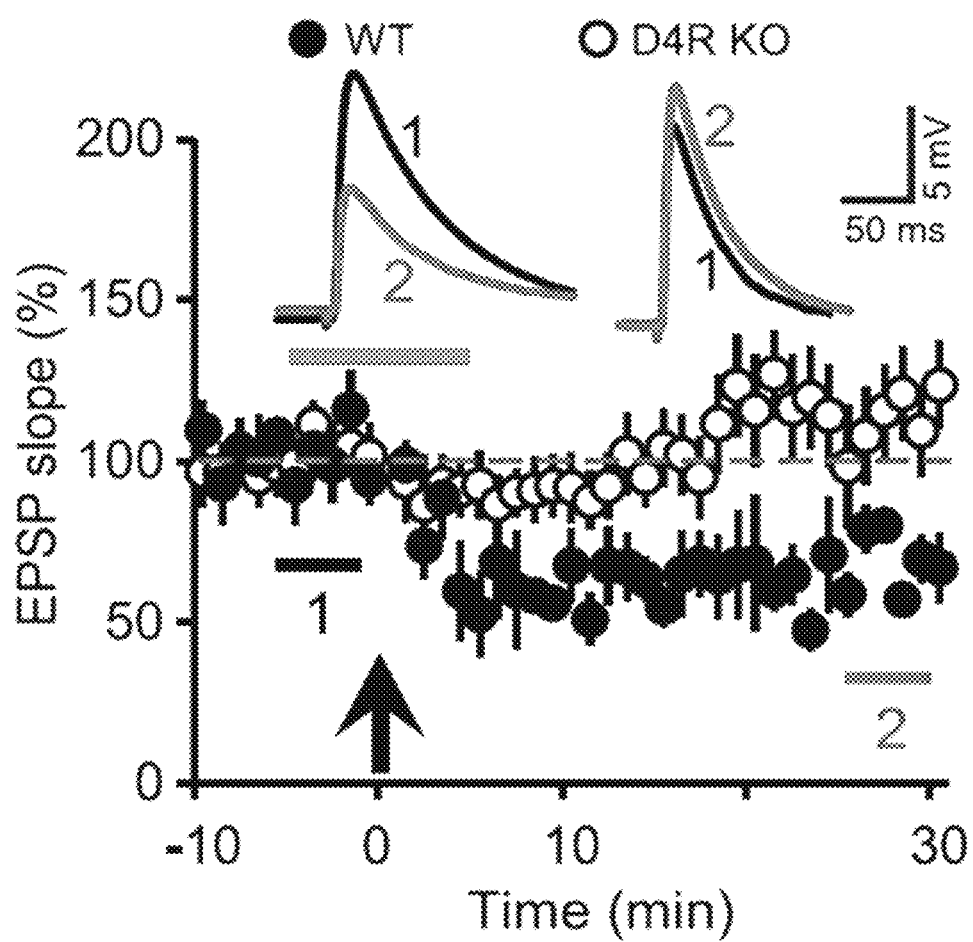
Figure 3F:
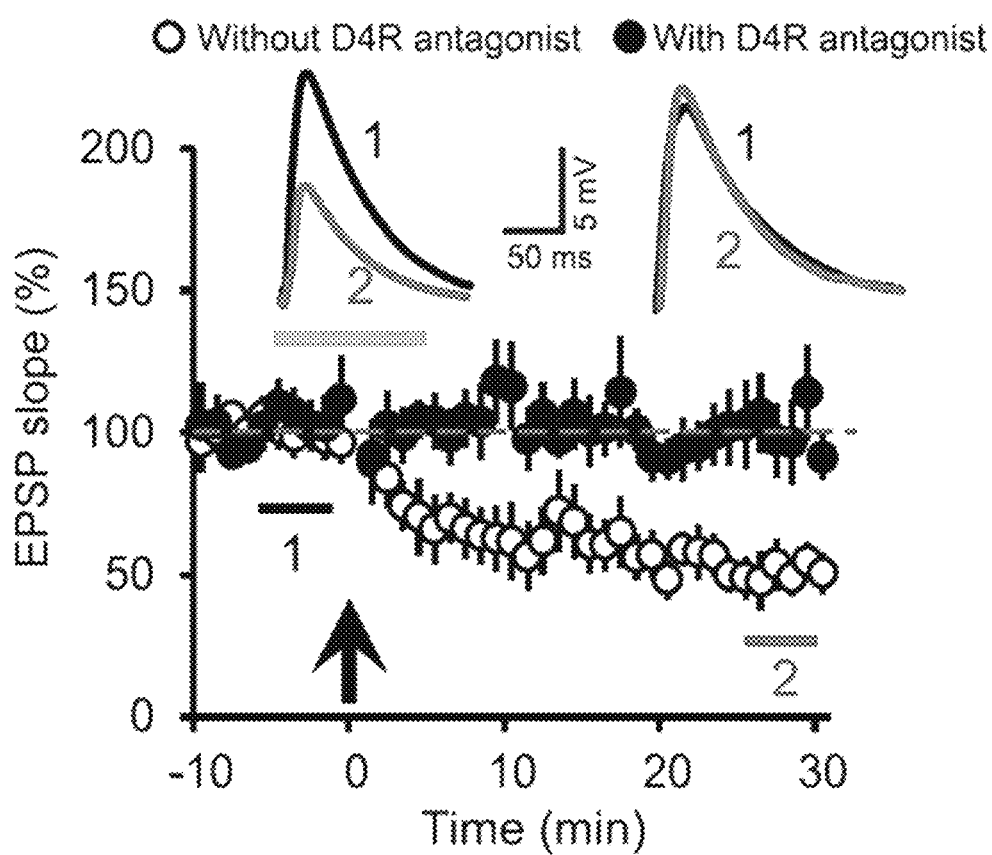

To exclude possible cross-reactivity of the pharmacological manipulation, we took advantage of a genetic model deficient in D4R. In D4R knockout (KO) mice, the same STDP protocol could not induce LTD despite the presence of DA (FIG. 3E). Importantly, L-745870 also interfered with the induction of LTD that had been normally induced after weak fear conditioning in wild-type (WT) mice, supporting the involvement of D4R (FIG. 3F).

Taken together, D4R is a major subtype of DA receptors required for the induction of DA-LTD, and its activation is likely to permit LTD in the dorsal ITC after weak fear conditioning.

D4R is expressed throughout brain regions including the amygdala, and the polymorphisms are implicated in various psychiatric disorders. Indeed, our immunohistochemistry revealed the presence of D4R in the dorsal ITC as well as other amygdale nuclei.

We also used structured illumination microscopy (SIM) over the dorsal ITC neurons to resolve colocalization of D4R with either synaptophysin, a marker for synaptic vesicles, or gephyrin, a marker for GABAergic postsynaptic density. This superresolution imaging indicated that D4R exhibited higher co-localization with synaptophysin than with gephyrin.

Figure 3G:
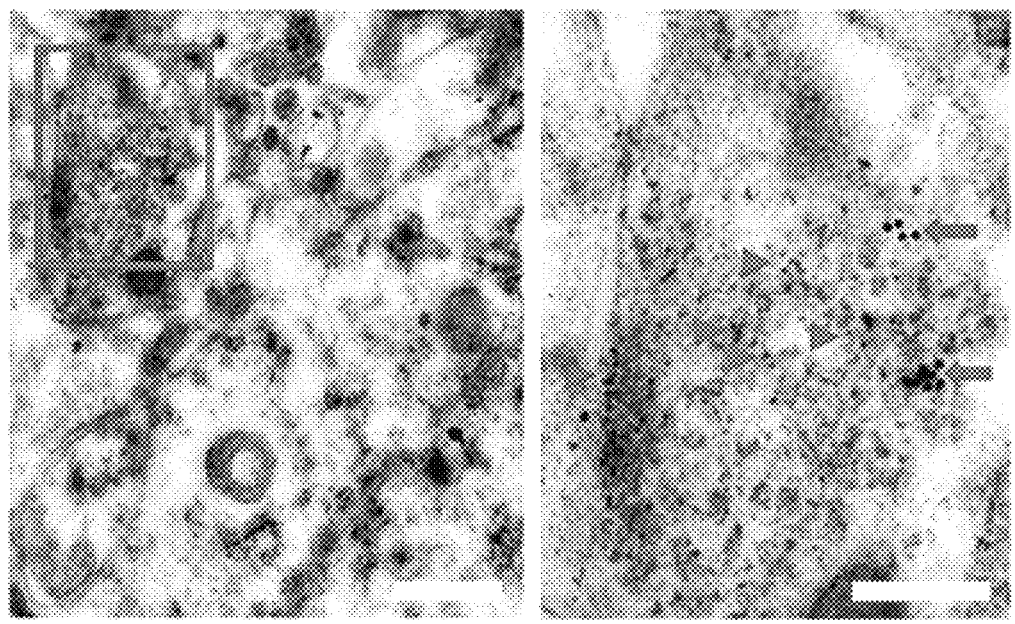
Figure 3H:
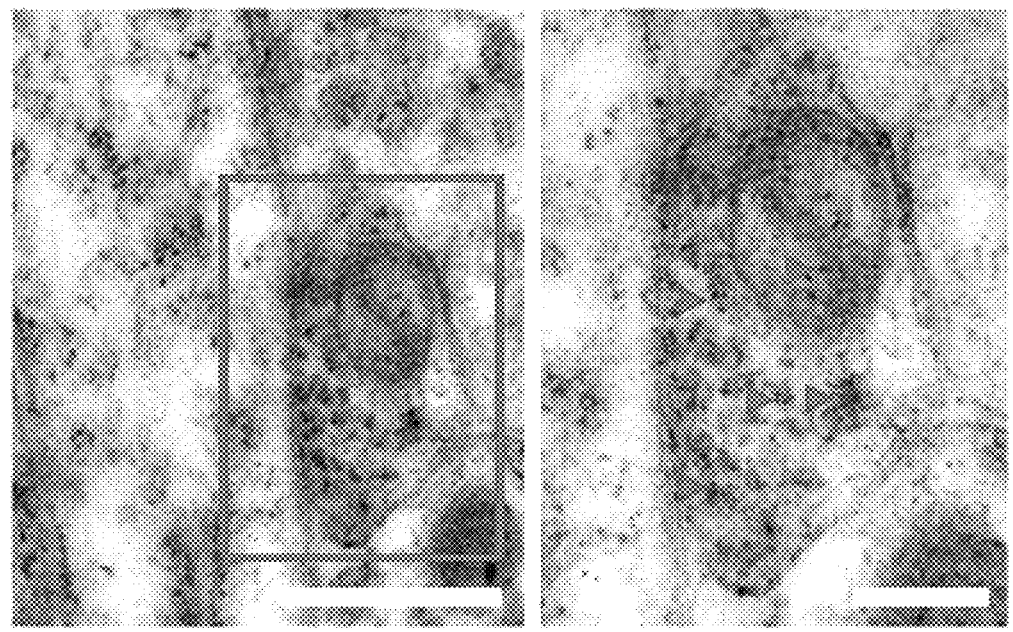

To analyze the subcellular localization of D4R, we performed post-embedding immuno-gold transmission electron microscopy. We detected D4R-bound gold particles in axon terminals of symmetric inhibitory synapses that were labeled with GAD67 and contacting the somas (FIG. 3G). In contrast, no D4R immunoreactivity was observed in GAD67-containing presynaptic terminals of D4R KO mice (FIG. 3H), as expected. Therefore, D4R appears to be present in the dorsal ITC synapses and predominantly distributed in GABAergic presynaptic terminals.

2-4. Feed-Forward Inhibition in the Dorsal ITC Leads to DA-LTD

Figure 4A:
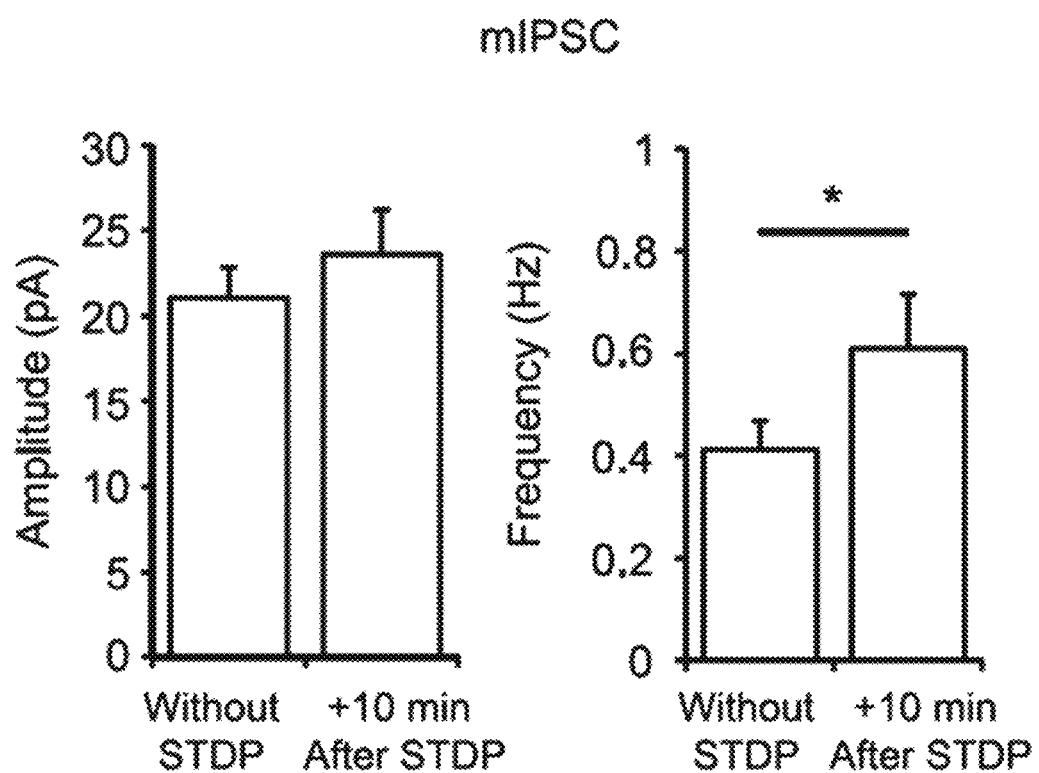
Figure 4B:
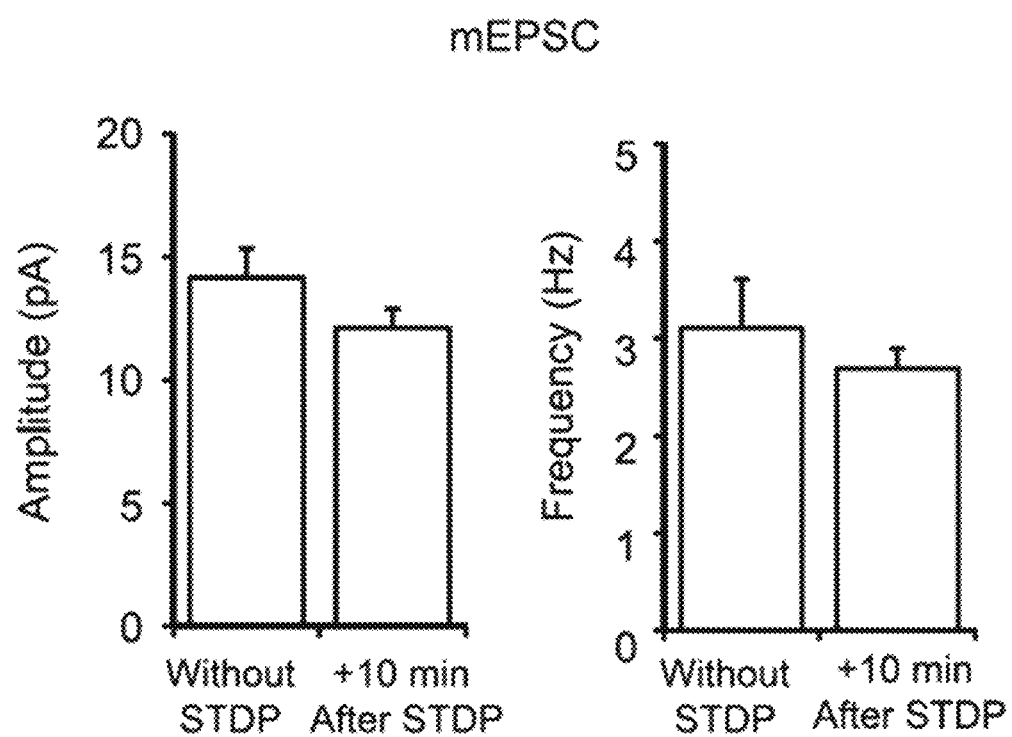

To elucidate the mechanistic bases of DA-LTD, we monitored basal transmission of the dorsal ITC synapses. After the induction of DA-LTD, mIPSC frequency significantly increased, whereas mEPSCs were unaffected (FIGS. 4A and 4B).

Figure 4C:
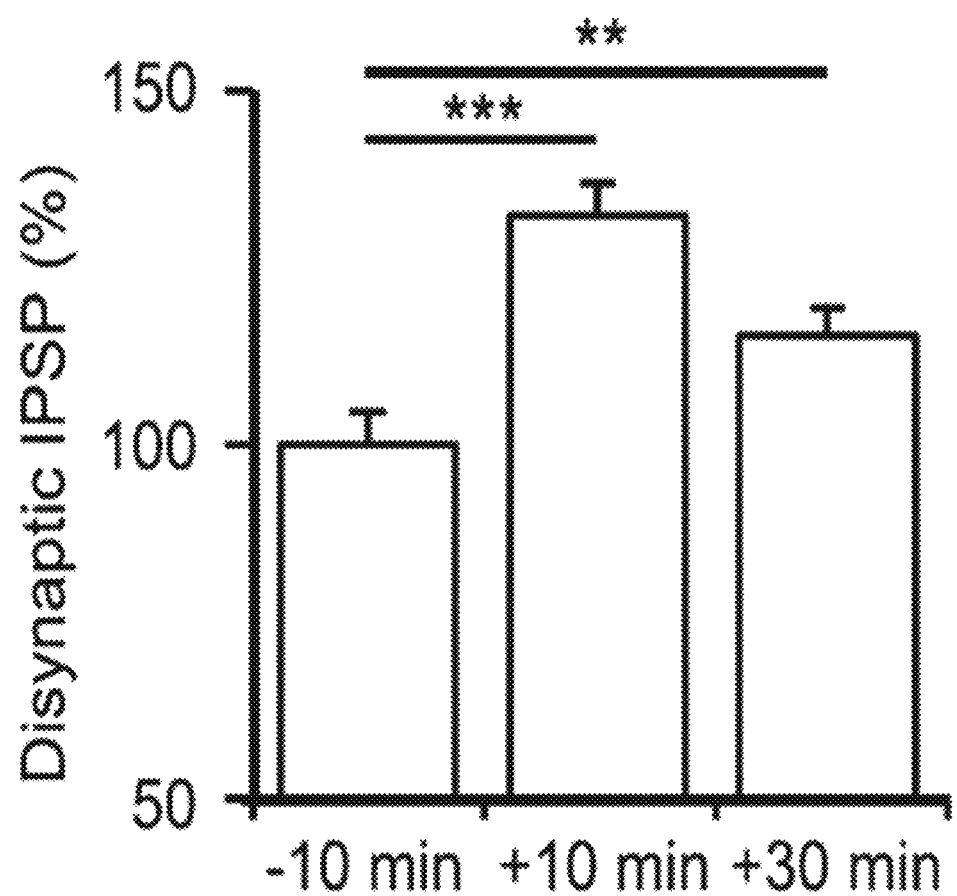

Interestingly, cumulative probability plots of mIPSCs revealed that both frequency and amplitude increased after DA-LTD, but those of mEPSCs did not change. We also detected significant increases in disynaptic IPSPs after DA-LTD induction (FIG. 4C), indicating enhanced feed-forward inhibition presumably from the neighboring dorsal ITC neurons.

Figure 4D:
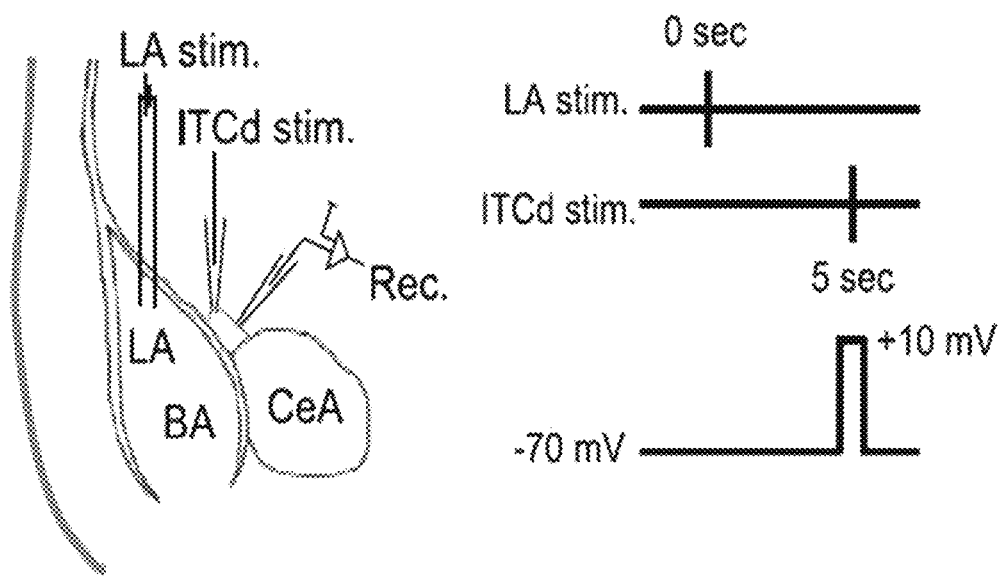

To corroborate an increase in GABAergic transmission within the dorsal ITC, we recorded postsynaptic currents (PSCs) from single ITC neurons while interleaving stimulation of LA or dorsal ITC areas (every 5 s) (FIG. 4D). Due to the small size of the dorsal ITC, monosynaptic IPSCs were evoked with glass electrodes, whereas EPSCs were evoked by stimulating the LA with standard metal electrodes.

Figure 4E:
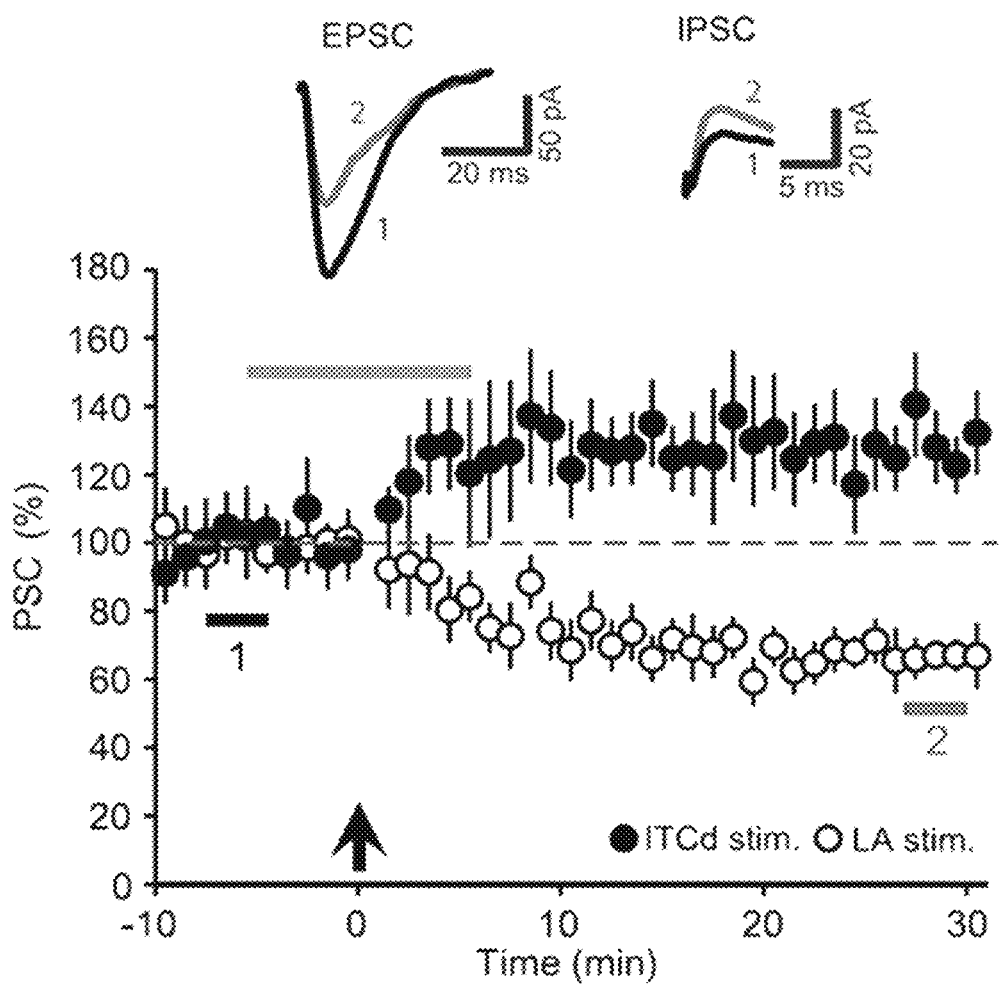

Notably, the latencies of postsynaptic currents evoked by stimulation of both the LA (2.78±0.19 ms) and the dorsal ITC (3.76±0.17 ms) were consistent with latencies of previously reported monosynaptic currents. Once DA-LTD was induced, IPSCs were potentiated while EPSCs were depressed (FIG. 4E). Presynaptic neurotransmitter release can be represented by the quantal content proportional to the inverse square of the coefficient of variation ($1/CV^2$) of evoked responses. Consistent with the enhanced presynaptic release of GABA, $1/CV^2$ increased for IPSCs, but not for EPSCs.

Figure 4F:
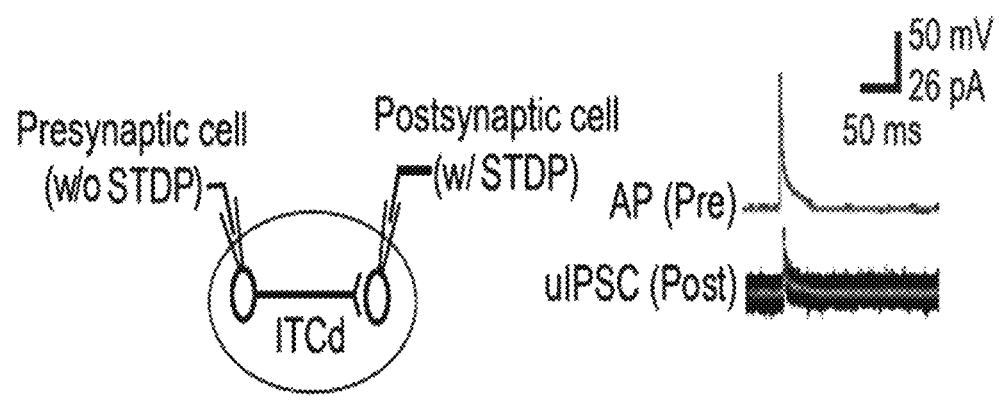
Figure 4G:
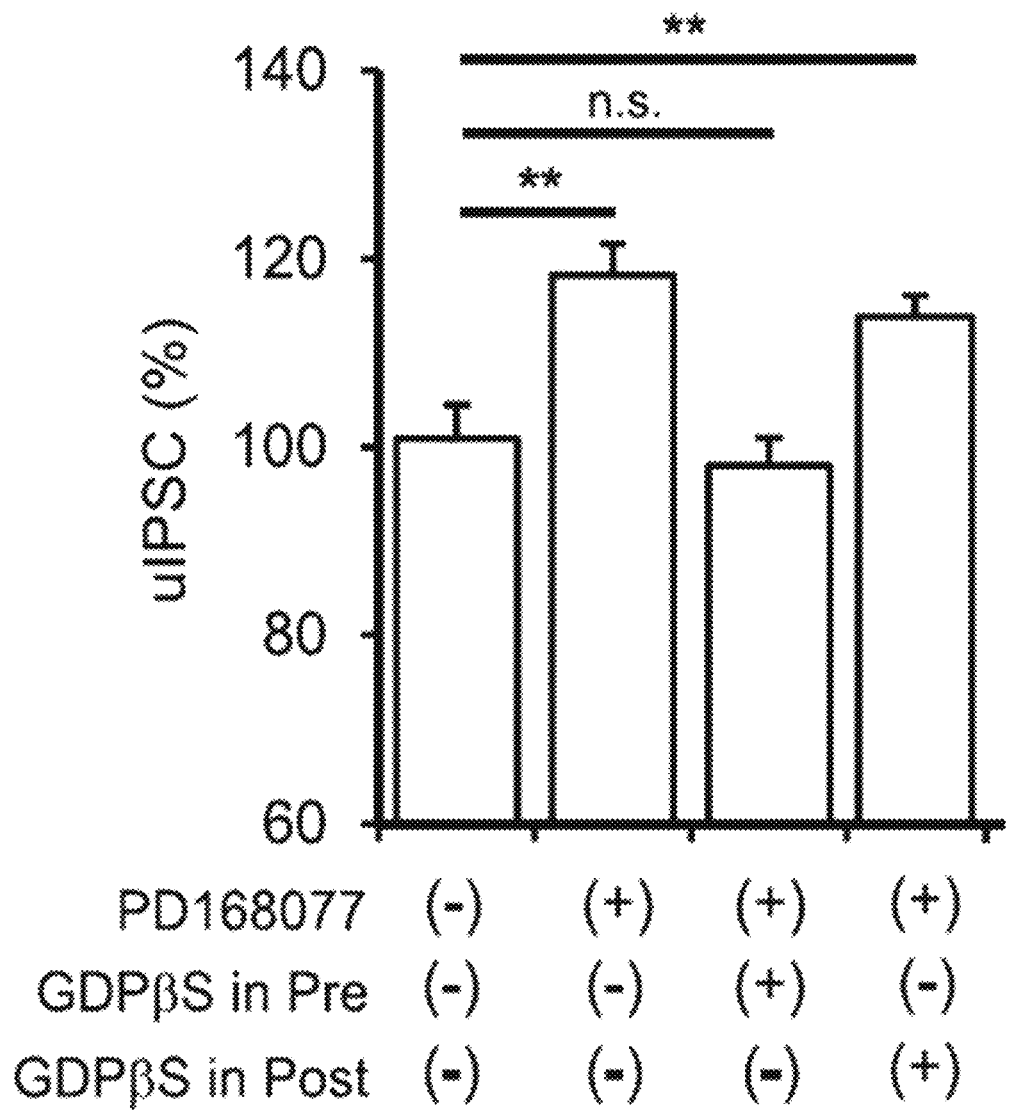

After synaptically coupled ITC neurons were identified with action potentials elicited by current injection and resultant outward IPSCs, we analyzed the unitary IPSCs (uIPSCs) by paired recording (FIG. 4F). The amplitude of uIPSCs markedly increased when LTD was induced by injecting currents to the postsynaptic ITC neurons while stimulating the LA in the presence of PD-168077 (FIG. 4G). Notably, the increase in the amplitude of uIPSCs was positively correlated with LTD magnitude, consistent with the causal role of GABA release for LTD (FIG. 4H).

Since D4R was enriched at presynaptic sites (FIG. 3G), we asked: does the increment of GABA release resulting from activation of presynaptic D4R contribute to LTD? To address this question, we selectively included GDPβS, an antagonist of G protein signaling in either presynaptic or postsynaptic ITC neurons. GDPβS blocked an LTD-induced increment of uIPSC amplitude when infused into the presynaptic ITC neurons, but not when infused into the postsynaptic ITC neurons (FIG. 4G).

Collectively, DA-LTD arose from the potentiation of GABAergic transmission in intrinsic circuits of the dorsal ITC, most likely by activation of presynaptic D4R.

Figure 5A:
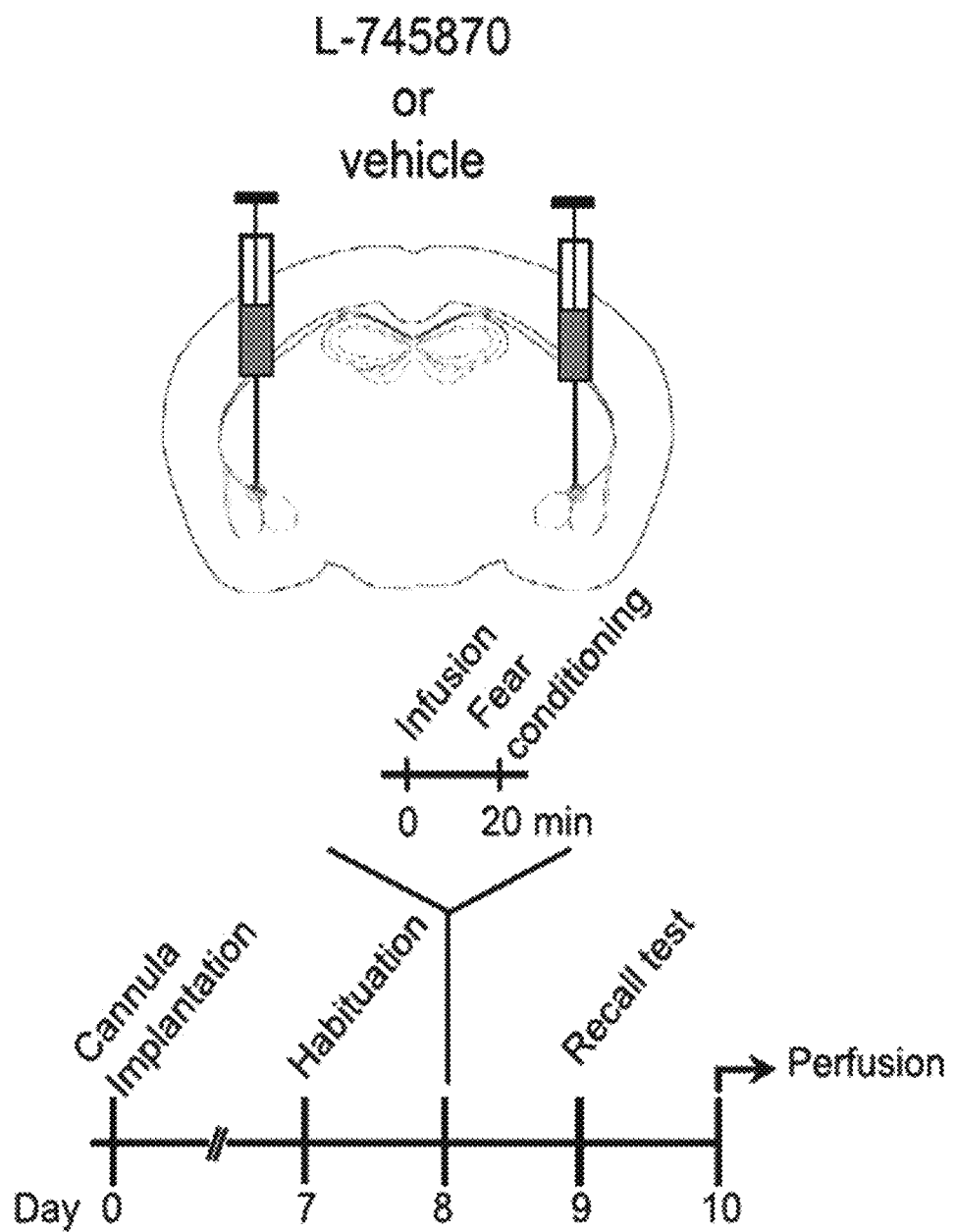

2-5. Blockade of D4R or Reversal of LTD is Sufficient to Increase the Expression of Fear If DA-LTD at the dorsal ITC is a synaptic mechanism that regulates neural circuits conveying fear memory, manipulation of D4R activity or synaptic plasticity at the dorsal ITC should affect fear memory. To test this hypothesis, we first examined the behavioral consequences of DA-LTD by pharmacological inactivation of D4R at the dorsal ITC. We injected either vehicle or L-745870 bilaterally into the dorsal ITC areas and then assessed acquisition and expression of fear memory (FIG. 5A).

Figure 5B:
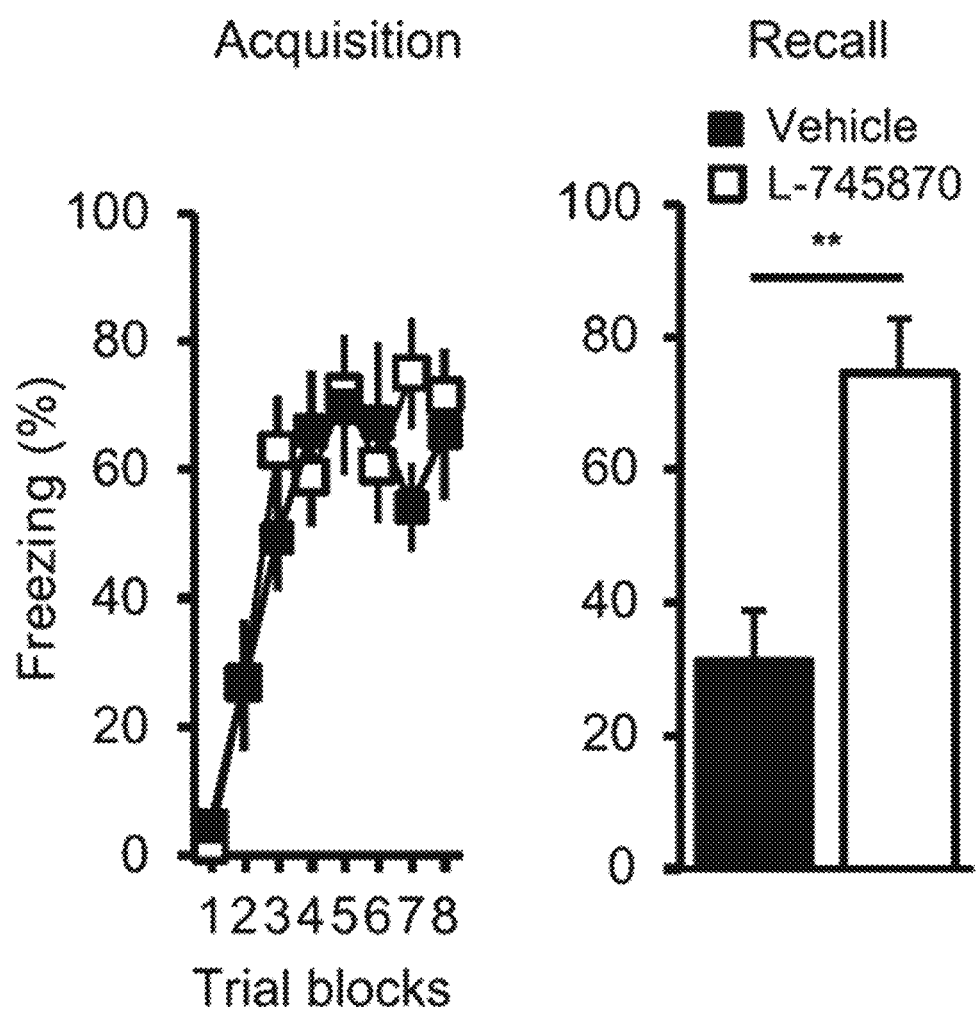

Animals that received either vehicle or L-745870 displayed comparable freezing levels during acquisition, which increased as the pairings of CS and US were repeatedly presented (FIG. 5B). When assessed at 24 hr after weak fear conditioning, L-745870-infused mice exhibited significantly higher levels of freezing compared with vehicle-infused animals (FIG. 5B), indicating the involvement of D4R activity for fear expression.

Figure 5C:
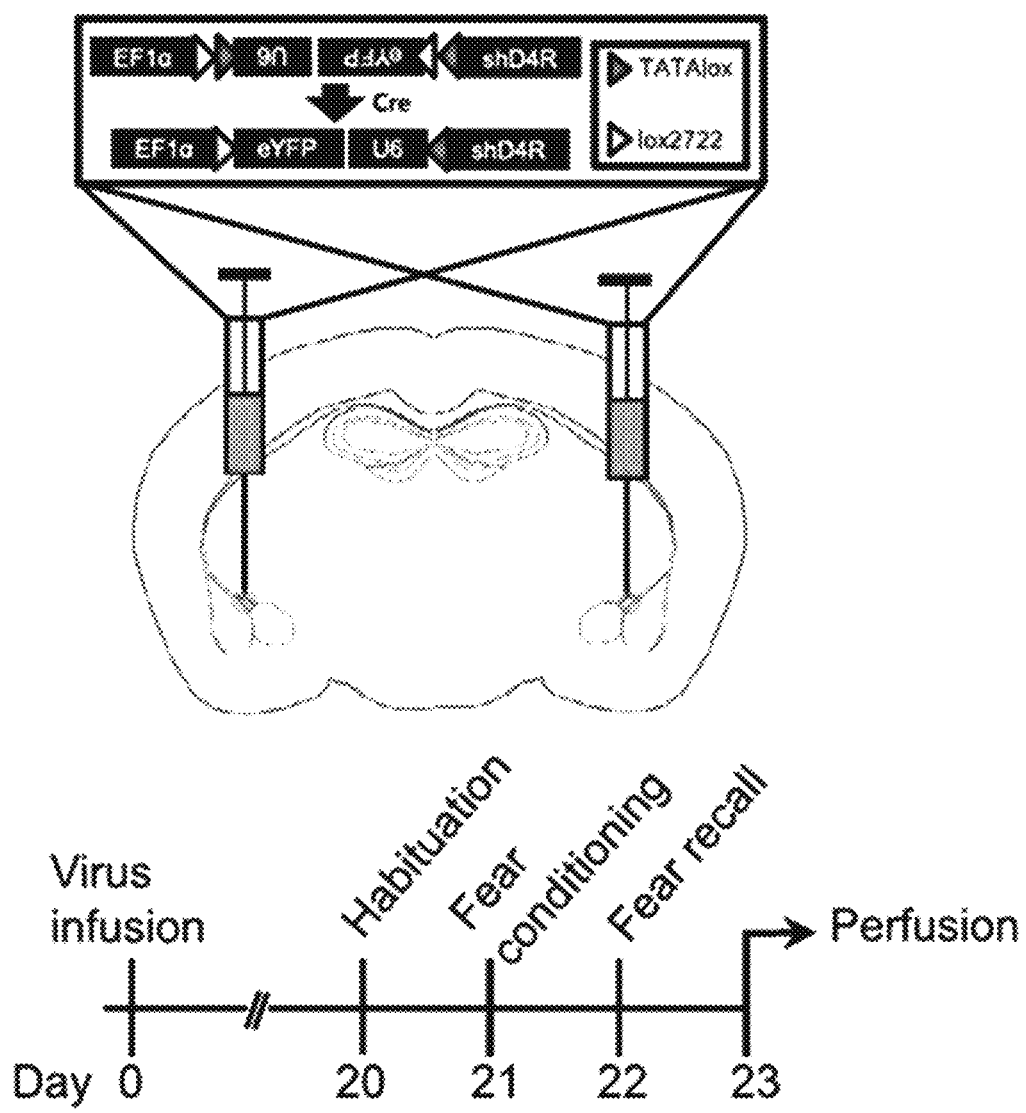
Figure 5D:
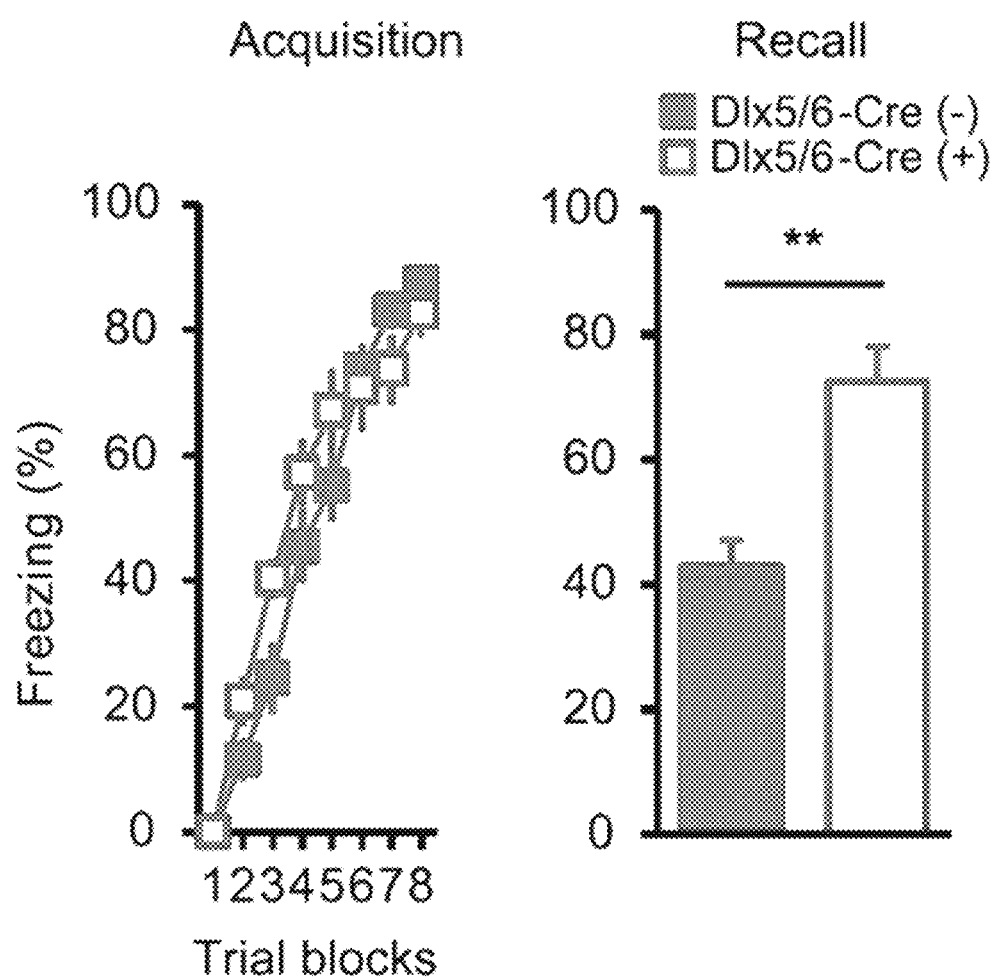
FIG. 5d shows the experimental result.

We next developed a new genetic method to deplete D4R in GABAergic neurons of the dorsal ITC. This viral vector enables us to knock down a given gene with small hairpin RNA (shRNA) and simultaneously identify those infected/knocked down neurons with expression of eYFP in a Cre-dependent manner. We infused the AAV containing shRNA for D4R (rAAV2-cKDeYFP-shD4R) into the dorsal ITC of Dlx5/6-Cre (−) or Dlx5/6-Cre (+) mice expressing Cre at GABAergic neurons (FIG. 5C).

eYFP was expressed mainly in the dorsal ITC area, and D4R was markedly depleted in the dorsal ITC of Dlx5/6-Cre (+) mice compared to that of Dlx5/6-Cre (−) controls. Importantly, Dlx5/6-Cre (+) mice that received rAAV2-cKD-eYFPshD4R displayed higher levels of freezing than Dlx5/6-Cre (−) mice, whereas freezing levels during the acquisition of fear memory were indistinguishable (FIG. 5D). Interestingly, WT and D4R KO mice did not differ in fear expression to weak fear conditioning, highlighting the importance of the dorsal ITC circuits for controlling fear expression.

The small size of the dorsal ITC makes it difficult to be completely certain that we localized the region-specific knockdown of D4R only to the dorsal ITC. However, it should be noted that we employed both pharmacological and genetic approaches for local manipulation of D4R with the same results.

Therefore, we provide evidence that D4R in the dorsal ITC neurons could, at least in part, be a functional prerequisite for limiting fear expression, especially to less-salient experience, and thus might delineate the integrity of fear memory.

2-6. Optogenetic Inhibition of LTD Induces Fear Expression

Figure 6A:
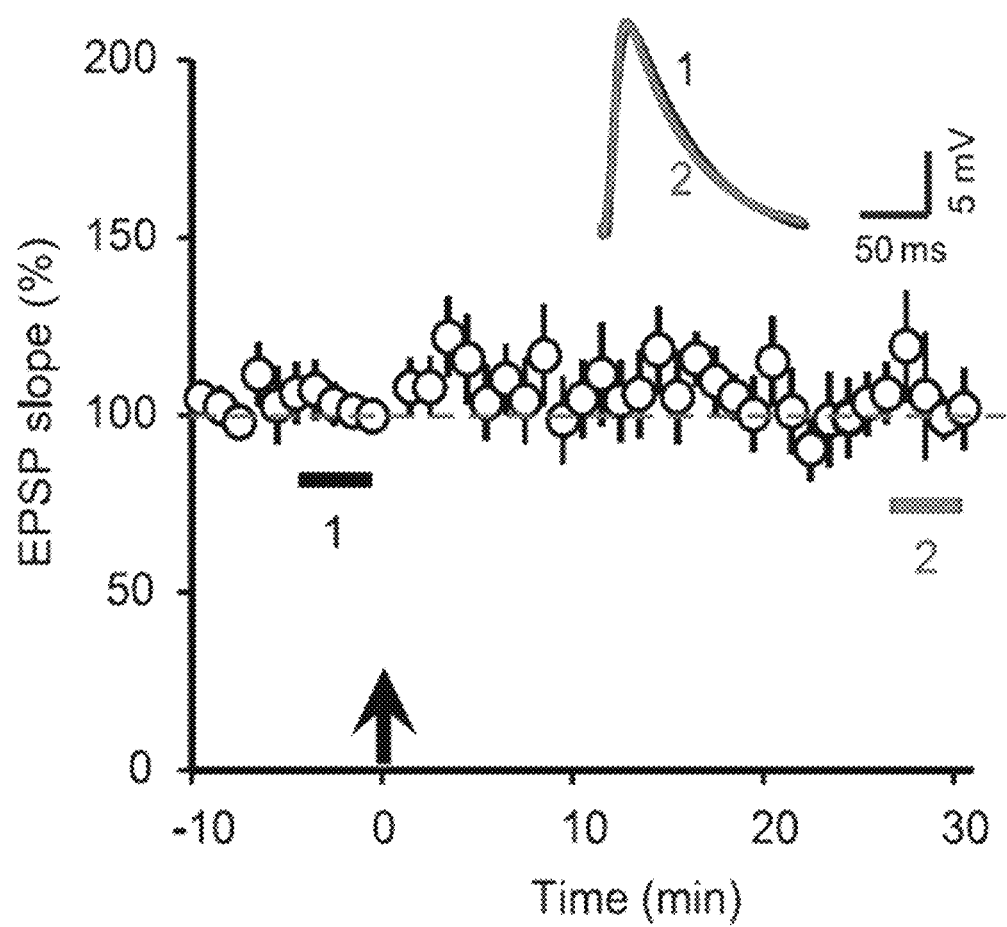

If synaptic plasticity in the dorsal ITC circuit was faithfully induced by the cues associated with weak fear conditioning, fear recall by cue exposure prior to recordings would affect the subsequent induction of LTD. Indeed, LTD was occluded when CS-induced recall was given to the fear-conditioned mice (FIG. 6A).

Figure 6B:
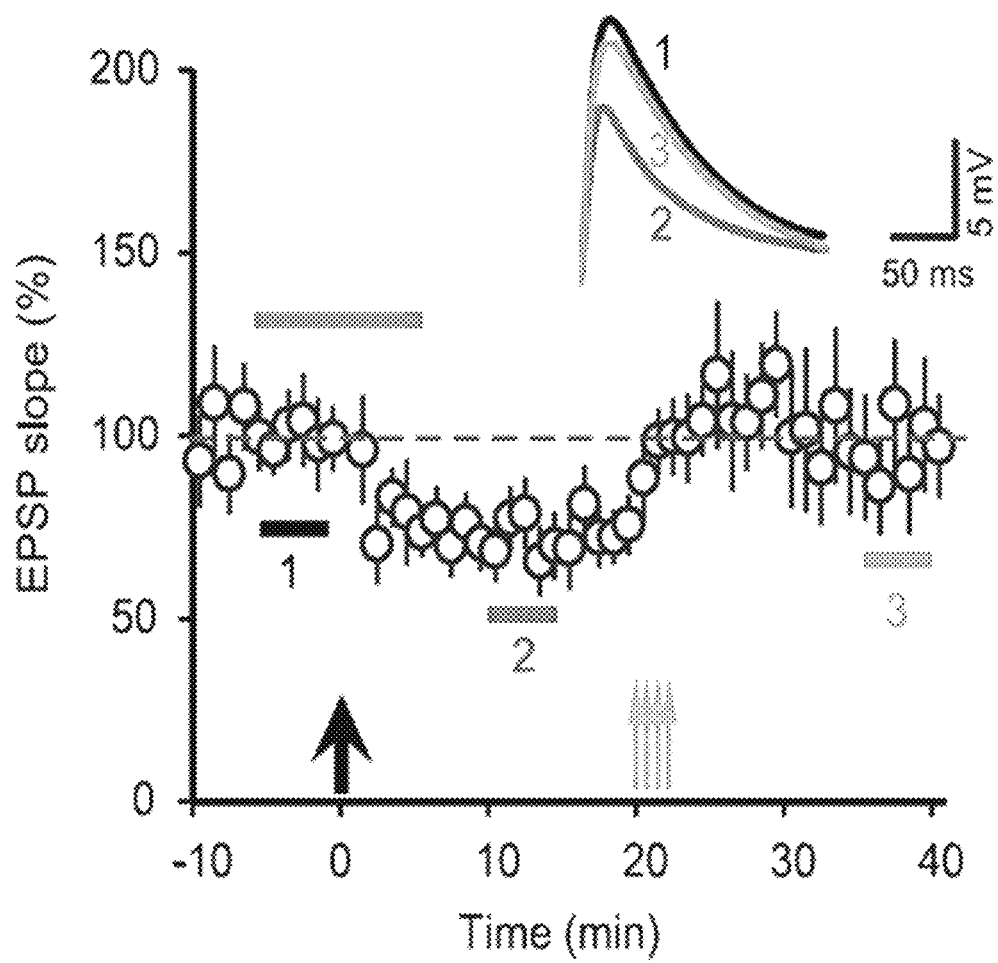

We surmised that fear expression could be altered if LTD is reversed in the LA-dorsal ITC pathway. We sought to optogenetically manipulate the LA-dorsal ITC pathway in order to abrogate LTD that normally arose after weak fear conditioning. In the amygdala slices from WT mice that received rAAV5-CamKIIa-hChR2-eYFP in LA, DA-LTD was abrogated by repeated light illumination mimicking theta burst stimulation (TBS) (FIG. 6B). It was shown that TBS induced N-methyl-Daspartic acid receptor (NMDAR)-dependent LTP in the LA-dorsal ITC pathway. We explored how optical TBS could affect DA-LTD and discovered that TBS-induced reversal of LTD also depended on NMDAR activity using its antagonist, 2-amino-5-phosphonopentanoic acid (APV).

Figure 6C:
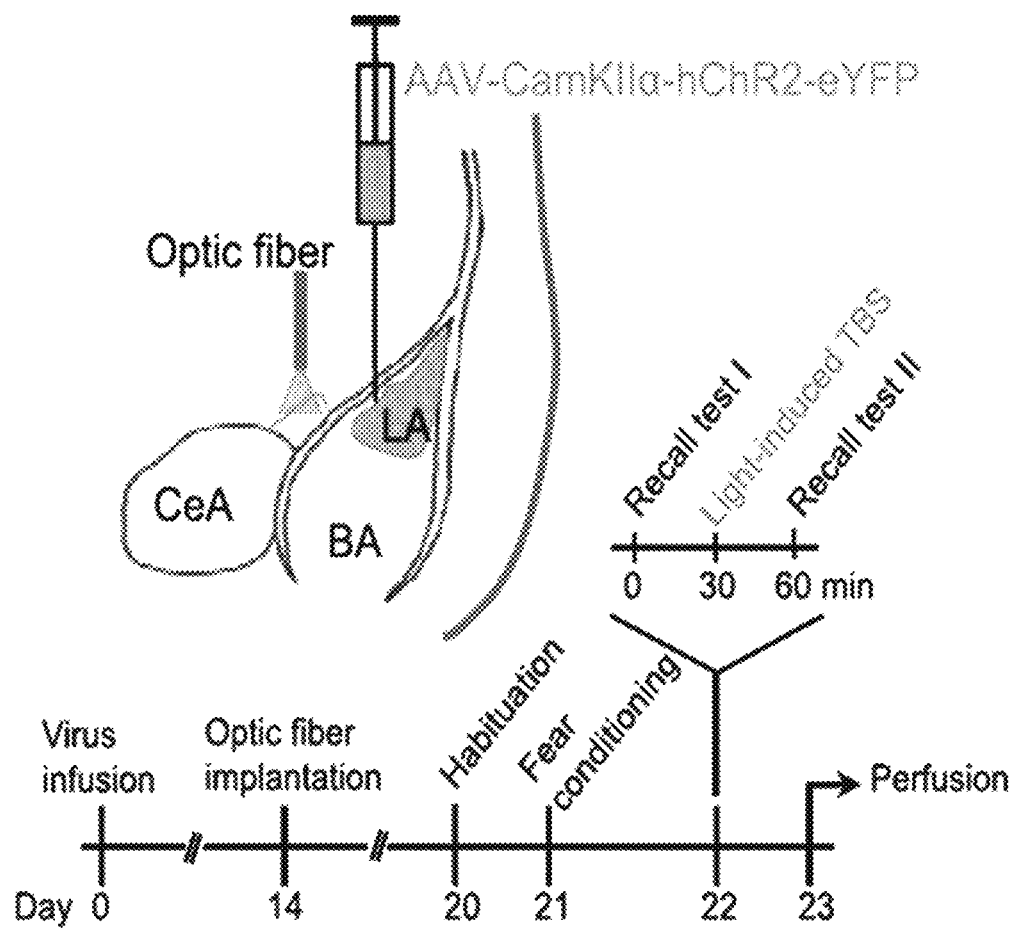
Figure 6D:
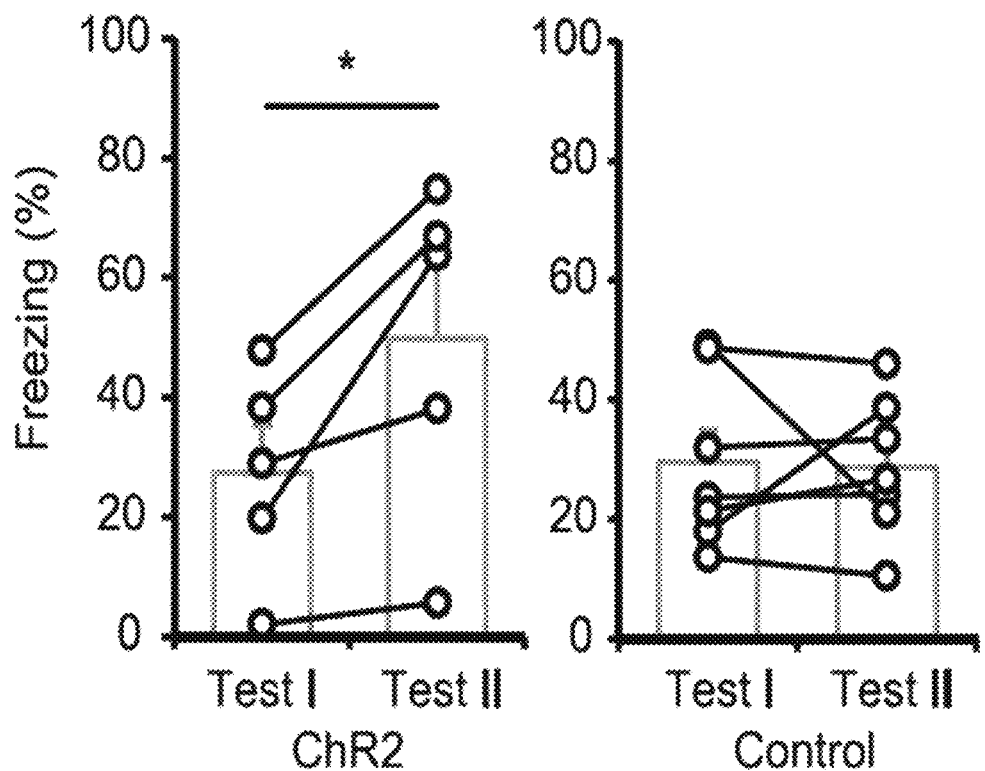

With optic fibers implanted at the top of the dorsal ITC, we applied optogenetic TBS and detected increased activity of the dorsal ITC neurons. When the optogenetic TBS was applied between fear recall tests (FIG. 6C), rAAV5-CamKIIa-hChR2-eYFP-infused mice displayed significant increases in freezing levels to the conditioned cue in the second recall test compared to those in the first test, whereas optogenetic TBS resulted in no behavioral changes in rAAV5-CamKIIa-eYFP-infused mice (FIG. 6D).

These results suggest that LTD at the dorsal ITC would be a critical cellular substrate that can limit learned fear.

2-7. Impaired LTD at the Dorsal ITC in a PTSD-Like Animal Model

Since both D4R blockade and reversal of LTD resulted in increased levels of fear expression, LTD could be affected in the dorsal ITC of PTSD models. While most of the animal models for PTSD have been produced by exposure to a variety of stresses, PTSD models can also be produced by administration of glucocorticoids. The PTSD-like impairment of fear memory could be represented with enhanced fear responses as well as incapability to discriminate between threat- and safeness-predicting stimuli.

Figure 7A:
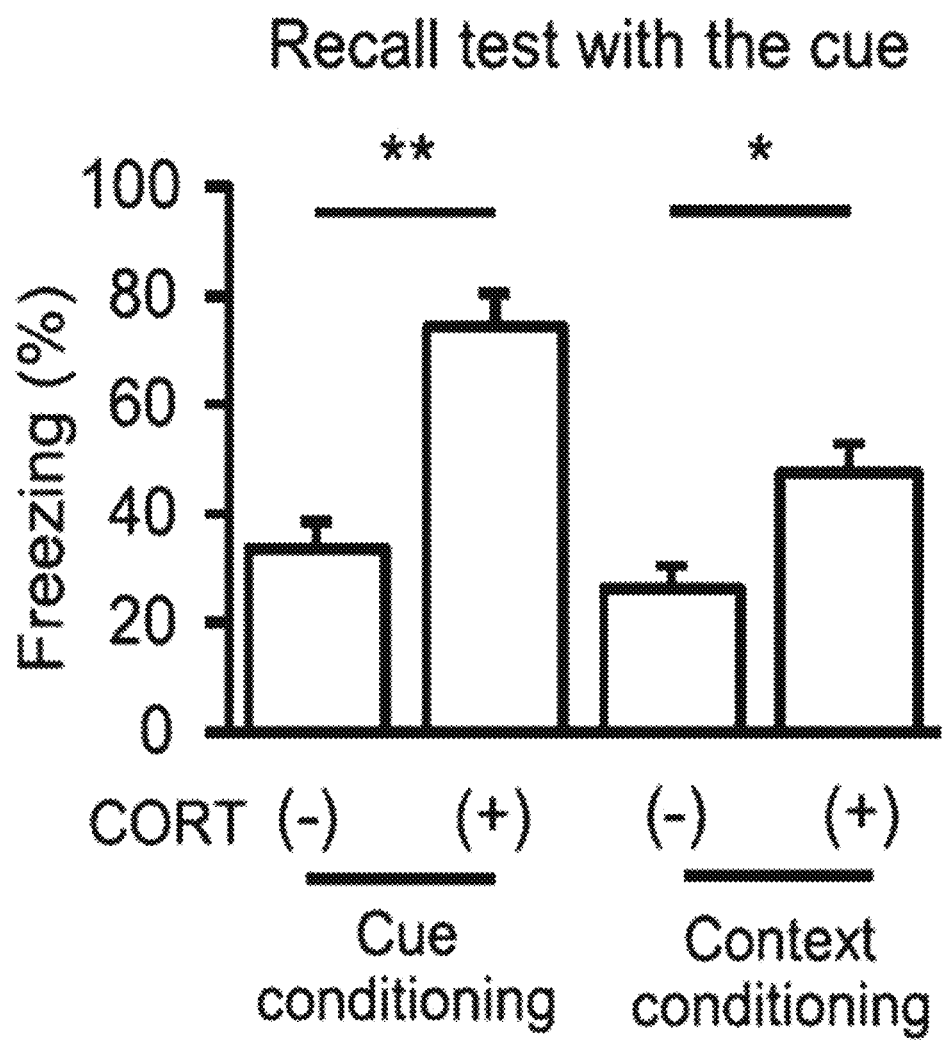
Figure 7B:
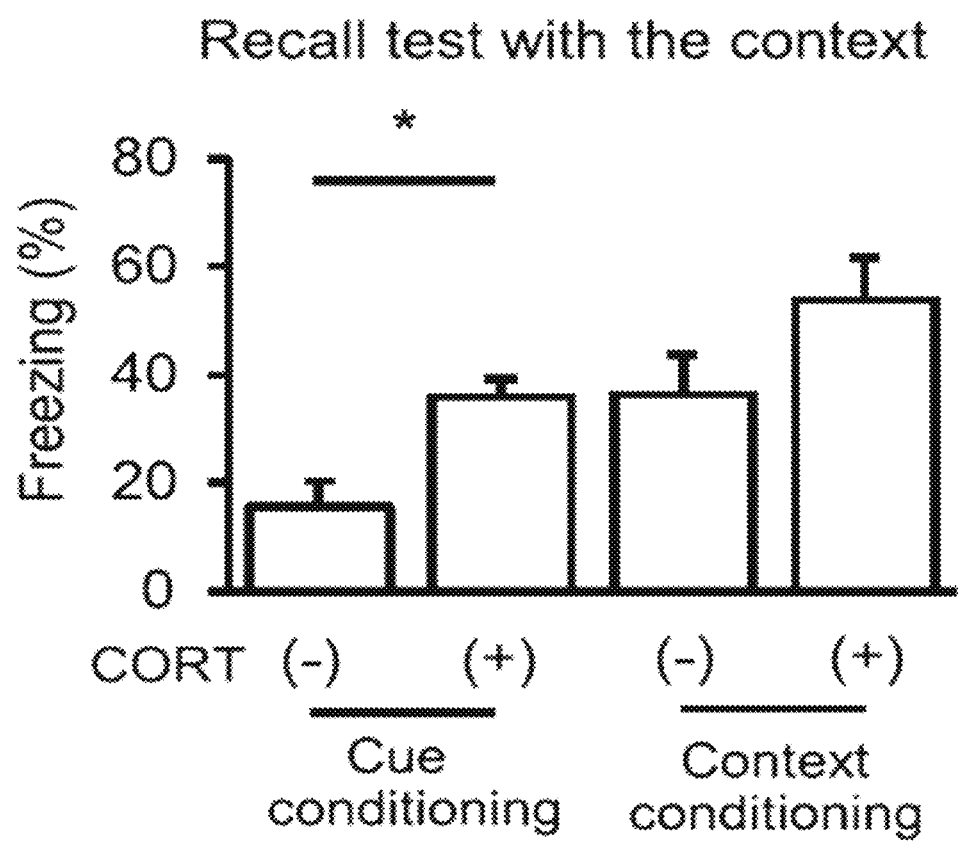

When we injected corticosterone (CORT; 5 mg/kg), a predominant form of glucocorticoid, into mice that underwent weak fear conditioning, PTSD-like impairment in fear memory was obviously observed; 24 hr after weak fear conditioning, the conditioned cue resulted in higher freezing levels in CORT-injected mice than in vehicle-injected animals, regardless of pairing the sub-threshold US with either the auditory cue or context (FIG. 7A). Importantly, the context also increased freezing levels in CORT-injected mice although they underwent only cue conditioning (FIG. 7B).

Figure 7C:
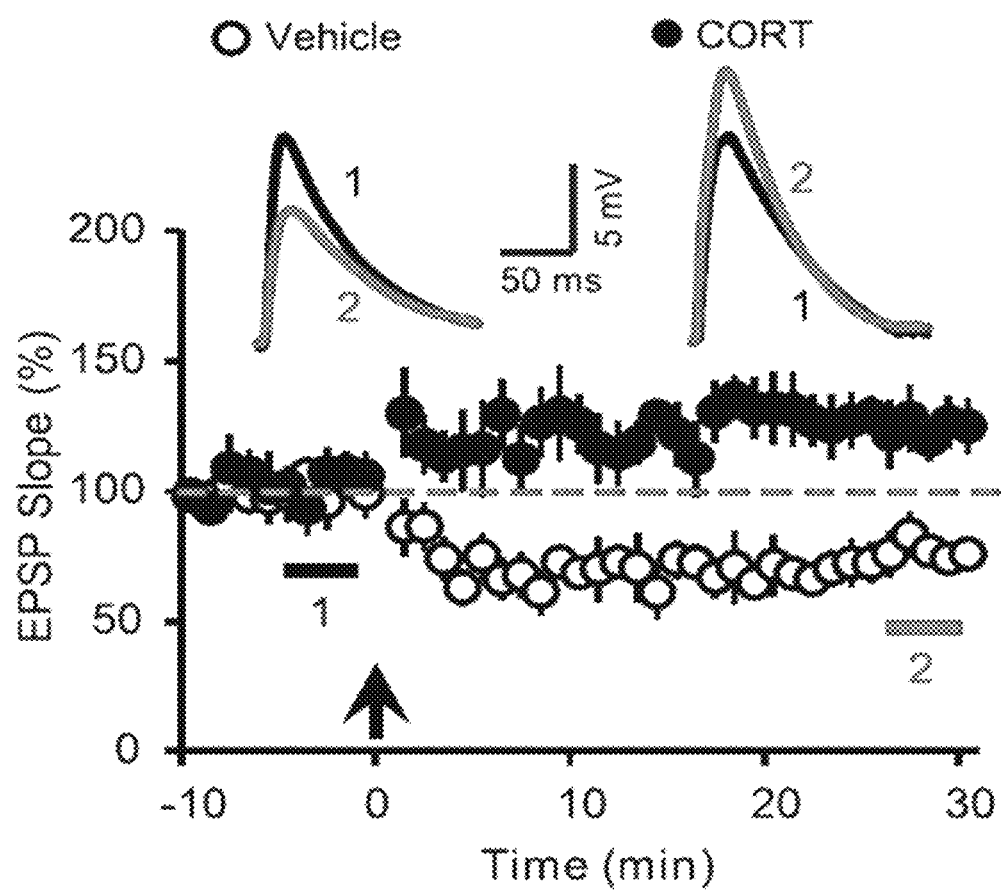

Subsequent to verification of PTSD-like impairment of fear memory in CORT-injected mice, we found that LTD could not be triggered in the dorsal ITC of CORT-treated mice, regardless of fear conditioning, whereas LTD was readily induced in vehicle-treated mice (FIG. 7C).

Interestingly, a glucocorticoid receptor antagonist RU38486 blocked both DA-LTD in naive mice and LTD in mice that underwent weak fear conditioning. These results prompted us to speculate that D4R elicits downstream signaling pathway(s) of glucocorticoid receptors.

Figure 7D:
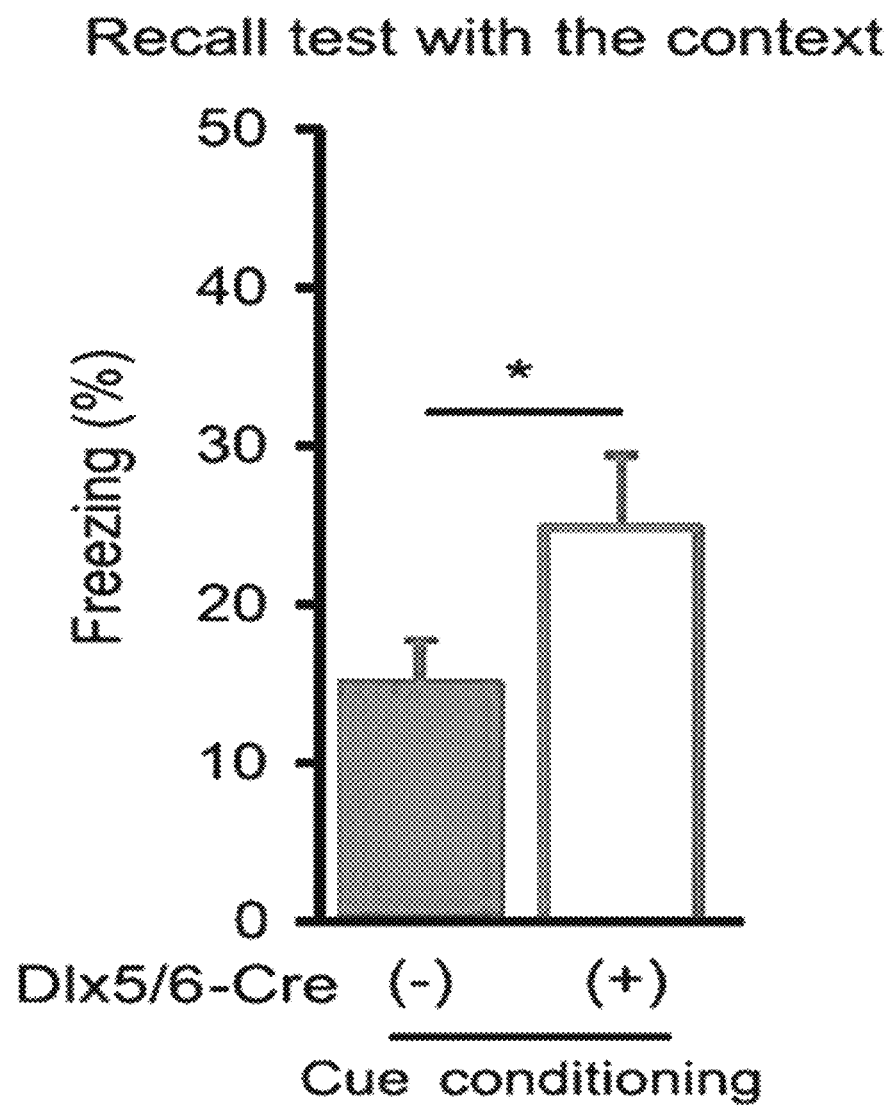

Consistent with functional overlapping of CORT- and D4R-triggered signaling, irrelevant context led to increased freezing levels in Dlx5/6-Cre (+) mice in which D4R was depleted in the dorsal ITC, compared with those in Dlx5/6-Cre (−) mice (FIG. 7D).

Figure 7E:
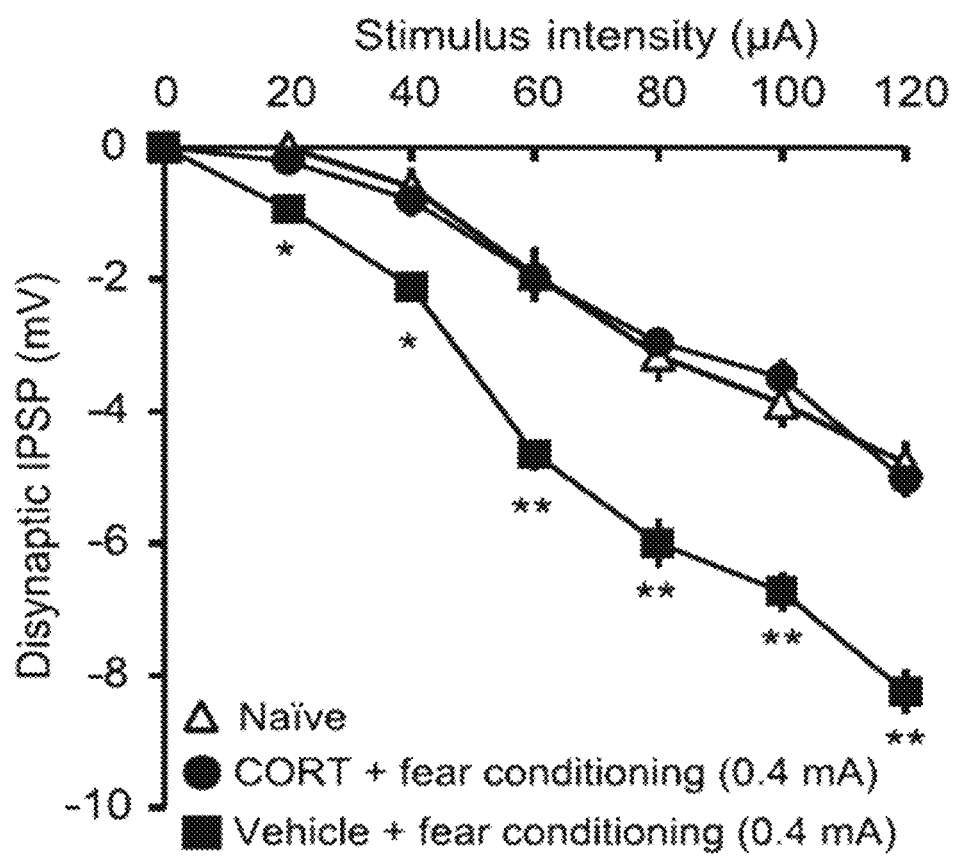

To obtain mechanistic insights into the LTD impairment, we constructed the input-output curves of evoked disynaptic IPSPs. The disynaptic IPSPs in CORT-treated mice were not altered after weak fear conditioning, whereas those in vehicle-treated mice significantly increased (FIG. 7E). Thus, the LTD deficit in CORT-treated mice appears to result from the impaired augmentation of inhibitory inputs to the dorsal ITC neurons.

2-8. Proposition of Possibility of Treating Posttraumatic Stress Disorder (PTSD)

The results of Examples 2-7 indicate that the abnormality of D4R mediated signaling and synaptic plasticity loss of an amygdala inhibitory circuit may cause post-traumatic stress disorder. Therefore, in Example 8, whether PTSD may be mitigated by treatment with an agonist of the dopamine receptor subtype 4 (D4R) in mice with PTSD-like symptoms was examined.

Figure 8:
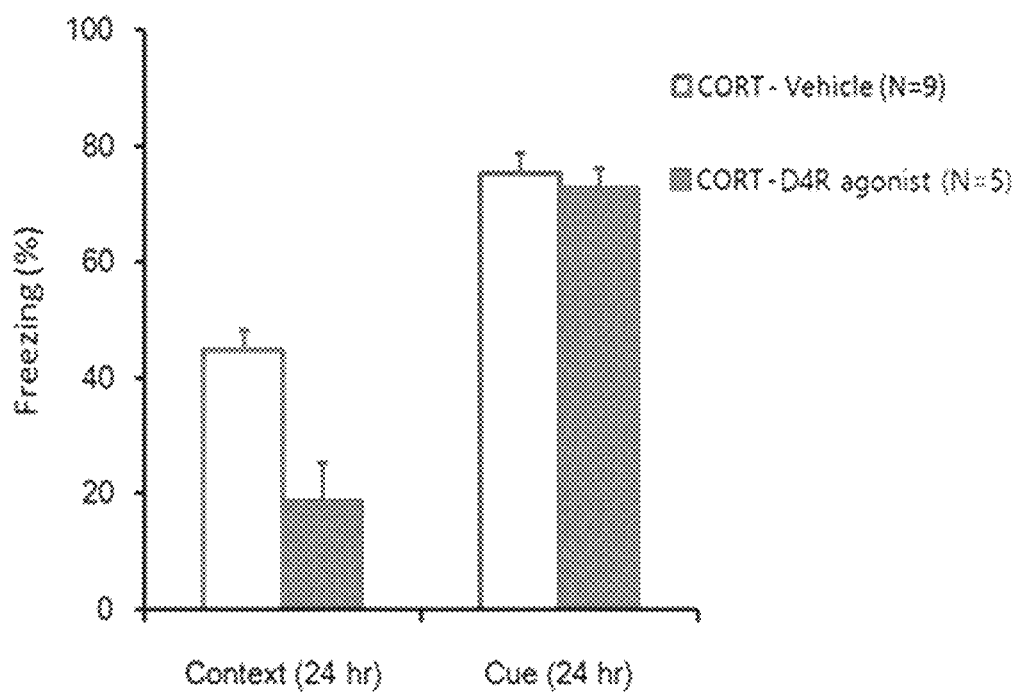
FIG. 8 shows that improved functions of a receptor result in the decreases in fear behavior responses due to treatment of mice exhibiting PTSD-like behavior with D4R agonists.

As shown in FIG. 8, cue fear-conditioned mice were treated with PD-168077 (N-([4-(2-cyanophenyl)piperazine-1-yl]methyl)-3-methylbenzamide) as an agonist of the D4R to increase the function of the receptor, from which it can be seen that fear behavioral reactions (freezing) was significantly reduced by 50% or more compared to a control (vehicle).

Therefore, the D4R agonist of the present invention can induce long-term synaptic depression (LTD) at the dorsal ITC of the amygdala to suppress fear reactions, and thus can be usefully used to prevent or treat PTSD.

According to the present invention, it has been revealed that a specific type of dopamine receptor is associated with a LTD-induced fear memory expression mechanism, and therefore the understanding of the pathogenesis of PTSD can be improved.

In addition, the present invention provides an animal model exhibiting PTSD-like clinical symptoms and a method for preparing the same, which can be applied in analyses of stability and effectiveness of a therapeutic agent for PTSD and screening of a therapeutic drug.

Further, a target disclosed in the present invention, D4R, is only expressed in a specific part of the brain at a low expression level, and since it is also less expressed in the amygdala, which is considered to be important in fear conditioning, the D4R is regarded as one of the therapeutic targets that can minimize side effects. Particularly, the D4R is a target based on a molecular mechanism for synaptic plasticity generated specific to circuits of an inhibitory neuronal cell population present in the amygdala, and thus a drug targeting D4R has a higher understanding of application thereof than those of conventional drugs.

Furthermore, since the D4R agonist of the present invention has been approved by the US FDA and clinically used for psychiatric diseases such as schizophrenia, it can be immediately used in clinical applications for PTSD symptoms.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A mouse comprising an exogenous polynucleotide comprising an inhibitory RNA (iRNA) that inactivates an endogenous dopamine receptor subtype 4 (D4R) gene in the dorsal intercalating cell mass (ITC) of the amygdala of the mouse, wherein the dorsal ITC of the mouse exhibits inhibited D4R expression (pg 11, line 17).

2. A method for making the mouse of claim 1, comprising: administering an inhibitory RNA (iRNA) that inactivates an endogenous dopamine receptor subtype 4 (D4R) gene directly into the dorsal intercalating cell mass (ITC) of the amygdala of the mouse such that the dorsal ITC of the mouse exhibits inhibited D4R expression.

* * * * *